United States Patent
Sengun et al.

(10) Patent No.: US 12,402,874 B2
(45) Date of Patent: *Sep. 2, 2025

(54) SURGICAL CONSTRUCTS WITH COLLAPSING SUTURE LOOP AND METHODS FOR SECURING TISSUE

(71) Applicant: Medos International Sàrl, Le Locle (CH)

(72) Inventors: Mehmet Ziya Sengun, Canton, MA (US); Howard C. Tang, Boston, MA (US); Gregory R. Whittaker, Stoneham, MA (US)

(73) Assignee: Medos International Sàrl, Le Locle (CH)

( * ) Notice: Subject to any disclaimer, the term of this patent is extended or adjusted under 35 U.S.C. 154(b) by 265 days.

This patent is subject to a terminal disclaimer.

(21) Appl. No.: 18/296,898

(22) Filed: Apr. 6, 2023

(65) Prior Publication Data
US 2023/0240674 A1 Aug. 3, 2023

Related U.S. Application Data

(60) Continuation of application No. 16/826,432, filed on Mar. 23, 2020, now Pat. No. 11,672,522, which is a
(Continued)

(51) Int. Cl.
*A61B 17/04* (2006.01)
*A61B 17/06* (2006.01)

(52) U.S. Cl.
CPC ...... *A61B 17/0401* (2013.01); *A61B 17/0469* (2013.01); *A61B 17/06166* (2013.01);
(Continued)

(58) Field of Classification Search
CPC ............ A61B 17/0401; A61B 17/0469; A61B 17/06166; A61B 2017/044;
(Continued)

(56) References Cited

U.S. PATENT DOCUMENTS

| 2,566,625 A | 9/1951 | Nagelmann |
|---|---|---|
| 2,600,395 A | 6/1952 | Domoj et al. |

(Continued)

FOREIGN PATENT DOCUMENTS

| AU | 724861 B2 | 10/2000 |
|---|---|---|
| AU | 2008229746 B2 | 3/2011 |

(Continued)

OTHER PUBLICATIONS

Adjacent Definition & Meaning, Merriam-Webster, https://www.merriam-webster.com/dictionary/adjacent, accessed Nov. 21, 2024 (Year 2024).
(Continued)

*Primary Examiner* — Richard G Louis
(74) *Attorney, Agent, or Firm* — Barnes & Thornburg LLP

(57) ABSTRACT

Surgical constructs and methods are provided for securing soft tissue to bone. One exemplary embodiment of a construct is formed from a suture filament and includes two terminal ends of filament and an intermediate portion disposed along at least a portion of a length extending between the terminal ends. The construct can have a first terminal end that is the first terminal end of the filament, and a second terminal end that includes a loop. The loop can be formed by disposing the second terminal end of the filament within a volume of a portion of the intermediate portion of the filament. In some disclosed methods, both terminal ends of the filament can be passed through tissue when performing soft tissue repairs. Various other embodiments of constructs and methods are provided, including constructs having two or more filaments associated with an anchor and methods of using such constructs.

23 Claims, 10 Drawing Sheets

Related U.S. Application Data continuation of application No. 15/648,068, filed on Jul. 12, 2017, now Pat. No. 10,631,848, which is a division of application No. 14/145,486, filed on Dec. 31, 2013, now Pat. No. 9,737,293.

(60) Provisional application No. 61/791,079, filed on Mar. 15, 2013.

(52) U.S. Cl.
CPC .  *A61B 2017/044* (2013.01); *A61B 2017/0446* (2013.01); *A61B 2017/0458* (2013.01); *A61B 2017/0477* (2013.01); *A61B 2017/06185* (2013.01)

(58) Field of Classification Search
CPC .... A61B 2017/0446; A61B 2017/0458; A61B 2017/0477; A61B 2017/06185
See application file for complete search history.

(56) References Cited

U.S. PATENT DOCUMENTS

| | | |
|---|---|---|
| 2,697,624 A | 12/1954 | Thomas et al. |
| 2,758,858 A | 8/1956 | Smith, Sr. |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,320,629 A | 6/1994 | Noda et al. |
| 5,374,278 A | 12/1994 | Chesterfield et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | Michael |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker, Jr. et al. |
| 5,645,850 A | 7/1997 | Bezwada et al. |
| 5,647,616 A | 7/1997 | Hamilton |
| 5,647,874 A | 7/1997 | Hayhurst |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,697,950 A | 12/1997 | Fucci et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 5,989,252 A | 11/1999 | Fumex |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,299,612 B1 | 10/2001 | Ouchi |
| 6,319,271 B1 | 11/2001 | Schwartz et al. |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,716,234 B2 | 4/2004 | Grafton et al. |
| 6,767,037 B2 | 7/2004 | Wenstrom, Jr. |
| 6,818,010 B2 | 11/2004 | Eichhorn et al. |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |

(56) References Cited

U.S. PATENT DOCUMENTS

| | | |
|---|---|---|
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,905,904 B2 | 3/2011 | Stone et al. |
| 7,959,650 B2 | 6/2011 | Kaiser et al. |
| 7,981,140 B2 | 7/2011 | Burkhart |
| 8,012,171 B2 | 9/2011 | Schmieding |
| 8,088,130 B2 | 1/2012 | Kaiser et al. |
| 8,088,146 B2 | 1/2012 | Wert et al. |
| 8,114,128 B2 | 2/2012 | Cauldwell et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,231,653 B2 | 7/2012 | Dreyfuss |
| 8,231,654 B2 | 7/2012 | Kaiser et al. |
| 8,323,316 B2 | 12/2012 | Maiorino et al. |
| 8,419,769 B2 | 4/2013 | Thal |
| 8,545,535 B2 | 10/2013 | Hirotsuka et al. |
| 8,608,758 B2 | 12/2013 | Singhatat et al. |
| 8,790,369 B2 | 7/2014 | Orphanos et al. |
| 8,790,370 B2 | 7/2014 | Spenciner et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,894,684 B2 | 11/2014 | Sengun |
| 8,974,495 B2 | 3/2015 | Hernandez et al. |
| 9,017,381 B2 | 4/2015 | Kaiser et al. |
| 9,034,013 B2 | 5/2015 | Sengun |
| 9,060,763 B2 | 6/2015 | Sengun |
| 9,060,764 B2 | 6/2015 | Sengun |
| 9,095,331 B2 | 8/2015 | Hernandez et al. |
| 9,179,908 B2 | 11/2015 | Sengun |
| 9,192,373 B2 | 11/2015 | Sengun |
| 9,198,653 B2 | 12/2015 | Sengun et al. |
| 9,271,716 B2 | 3/2016 | Sengun |
| 9,345,468 B2 | 5/2016 | Sengun et al. |
| 9,345,567 B2 | 5/2016 | Sengun |
| 9,393,007 B2 | 7/2016 | Darois et al. |
| 9,510,819 B2 | 12/2016 | Stone et al. |
| 9,532,778 B2 | 1/2017 | Sengun et al. |
| 9,737,293 B2 | 8/2017 | Sengun et al. |
| 9,757,116 B2 | 9/2017 | Sengun |
| 9,763,655 B2 | 9/2017 | Sengun |
| 9,795,373 B2 | 10/2017 | Sengun |
| 9,833,229 B2 | 12/2017 | Hernandez et al. |
| 9,872,678 B2 | 1/2018 | Spenciner et al. |
| 9,895,145 B2 | 2/2018 | Sengun et al. |
| 10,258,321 B2 | 4/2019 | Sengun |
| 10,271,833 B2 | 4/2019 | Sengun |
| 10,292,695 B2 | 5/2019 | Sengun et al. |
| 10,524,777 B2 | 1/2020 | Sengun |
| 10,631,848 B2 | 4/2020 | Sengun et al. |
| 10,695,047 B2 | 6/2020 | Sengun |
| 10,736,624 B2 | 8/2020 | Sauer |
| 10,751,041 B2 | 8/2020 | Spenciner et al. |
| 10,835,231 B2 | 11/2020 | Hernandez et al. |
| 10,912,549 B2 | 2/2021 | Sengun et al. |
| 11,039,827 B2 | 6/2021 | Sengun et al. |
| 11,272,915 B2 | 3/2022 | Sengun |
| 11,672,522 B2 * | 6/2023 | Sengun ............ A61B 17/06166 606/232 |
| 11,672,523 B2 | 6/2023 | Sengun |
| 11,771,414 B2 | 10/2023 | Spenciner et al. |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0023268 A1 | 1/2003 | Lizardi |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0199185 A1 | 10/2004 | Davignon |
| 2004/0236373 A1 | 11/2004 | Anspach, III |
| 2005/0033363 A1 | 2/2005 | Bojarski et al. |
| 2005/0119696 A1 | 6/2005 | Walters et al. |
| 2005/0137624 A1 | 6/2005 | Fallman |
| 2005/0165416 A1 | 7/2005 | Bojarski et al. |
| 2005/0187577 A1 | 8/2005 | Selvitelli et al. |
| 2005/0251208 A1 | 11/2005 | Elmer et al. |
| 2006/0106423 A1 | 5/2006 | Welsel et al. |
| 2006/0178680 A1 | 8/2006 | Nelson et al. |
| 2006/0178702 A1 | 8/2006 | Pierce et al. |
| 2006/0259076 A1 | 11/2006 | Burkhart et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1 | 3/2007 | Dreyfuss |
| 2007/0083236 A1 | 4/2007 | Sikora et al. |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0239209 A1 | 10/2007 | Fallman |
| 2007/0255317 A1 | 11/2007 | Fanton et al. |
| 2008/0009901 A1 | 1/2008 | Redmond et al. |
| 2008/0009904 A1 | 1/2008 | Bourque et al. |
| 2008/0027446 A1 | 1/2008 | Stone et al. |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208253 A1 | 8/2008 | Dreyfuss et al. |
| 2008/0208265 A1 | 8/2008 | Frazier et al. |
| 2008/0228265 A1 | 9/2008 | Spence et al. |
| 2008/0255613 A1 | 10/2008 | Kaiser et al. |
| 2008/0275469 A1 | 11/2008 | Fanton et al. |
| 2008/0312689 A1 | 12/2008 | Denham et al. |
| 2009/0023984 A1 | 1/2009 | Stokes et al. |
| 2009/0036905 A1 | 2/2009 | Schmieding |
| 2009/0043317 A1 | 2/2009 | Cavanaugh et al. |
| 2009/0054928 A1 | 2/2009 | Denham et al. |
| 2009/0062850 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0082807 A1 | 3/2009 | Miller et al. |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0149883 A1 | 6/2009 | Brunsvold |
| 2009/0234387 A1 | 9/2009 | Miller et al. |

(56) References Cited

U.S. PATENT DOCUMENTS

| | | |
|---|---|---|
| 2009/0281568 A1 | 11/2009 | Cendan et al. |
| 2009/0281581 A1 | 11/2009 | Berg |
| 2009/0287246 A1 | 11/2009 | Cauldwell et al. |
| 2009/0306711 A1 | 12/2009 | Stone et al. |
| 2009/0312776 A1 | 12/2009 | Kaiser et al. |
| 2009/0312794 A1 | 12/2009 | Nason et al. |
| 2009/0318958 A1 | 12/2009 | Ochia |
| 2010/0004683 A1 | 1/2010 | Hoof et al. |
| 2010/0016892 A1 | 1/2010 | Kaiser et al. |
| 2010/0094425 A1 | 4/2010 | Bentley et al. |
| 2010/0162882 A1 | 7/2010 | Shakespeare |
| 2010/0204730 A1 | 8/2010 | Maiorino et al. |
| 2010/0249809 A1 | 9/2010 | Singhatat et al. |
| 2010/0249834 A1 | 9/2010 | Dreyfuss |
| 2010/0256677 A1 | 10/2010 | Albertorio et al. |
| 2010/0292732 A1 | 11/2010 | Hirotsuka et al. |
| 2010/0292792 A1 | 11/2010 | Stone et al. |
| 2011/0022083 A1 | 1/2011 | DiMatteo et al. |
| 2011/0022084 A1 | 1/2011 | Sengun et al. |
| 2011/0077667 A1 | 3/2011 | Singhatat et al. |
| 2011/0098727 A1 | 4/2011 | Kaiser et al. |
| 2011/0152928 A1 | 6/2011 | Colleran et al. |
| 2011/0190815 A1 | 8/2011 | Saliman |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0238111 A1 | 9/2011 | Frank |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0101523 A1 | 4/2012 | Wert et al. |
| 2012/0101524 A1 | 4/2012 | Bennett |
| 2012/0130423 A1 | 5/2012 | Sengun et al. |
| 2012/0130424 A1 | 5/2012 | Sengun et al. |
| 2012/0150223 A1 | 6/2012 | Manos et al. |
| 2012/0296375 A1 | 11/2012 | Thal |
| 2013/0110165 A1 | 5/2013 | Burkhart et al. |
| 2013/0158598 A1 | 6/2013 | Lizardi |
| 2013/0253581 A1 | 9/2013 | Robison |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2013/0296934 A1 | 11/2013 | Sengun |
| 2014/0039551 A1 | 2/2014 | Donahue |
| 2014/0081324 A1 | 3/2014 | Sengun |
| 2014/0107701 A1 | 4/2014 | Lizardi et al. |
| 2014/0188163 A1 | 7/2014 | Sengun |
| 2014/0188164 A1 | 7/2014 | Sengun |
| 2014/0277121 A1 | 9/2014 | Pilgeram et al. |
| 2014/0277132 A1 | 9/2014 | Sengun et al. |
| 2014/0330312 A1 | 11/2014 | Spenciner et al. |
| 2014/0343606 A1 | 11/2014 | Hernandez et al. |
| 2014/0343607 A1 | 11/2014 | Sengun et al. |
| 2015/0012038 A1 | 1/2015 | Sengun et al. |
| 2015/0025572 A1 | 1/2015 | Sengun |
| 2015/0045832 A1 | 2/2015 | Sengun |
| 2015/0238183 A1 | 8/2015 | Sengun |
| 2015/0245832 A1 | 9/2015 | Sengun |
| 2015/0297214 A1 | 10/2015 | Hernandez et al. |
| 2015/0313587 A1 | 11/2015 | Lizardi et al. |
| 2016/0128687 A1 | 5/2016 | Sengun |
| 2016/0278761 A1 | 9/2016 | Sengun et al. |
| 2016/0296222 A1 | 10/2016 | Sengun |
| 2017/0000479 A1 | 1/2017 | Sengun et al. |
| 2017/0303913 A1 | 10/2017 | Sengun et al. |
| 2017/0360428 A1 | 12/2017 | Sengun |
| 2017/0367690 A1 | 12/2017 | Sengun |
| 2018/0042600 A1 | 2/2018 | Hernandez et al. |
| 2018/0098763 A1 | 4/2018 | Spenciner et al. |
| 2018/0140292 A1 | 5/2018 | Sengun et al. |
| 2019/0216457 A1 | 7/2019 | Sengun |
| 2019/0223857 A1 | 7/2019 | Sengun |
| 2019/0223860 A1 | 7/2019 | Sengun et al. |
| 2020/0178952 A1 | 6/2020 | Sengun |
| 2020/0383681 A1 | 12/2020 | Sengun et al. |
| 2021/0030411 A1 | 2/2021 | Spenciner et al. |
| 2021/0038214 A1 | 2/2021 | Sengun |
| 2021/0093312 A1 | 4/2021 | Hernandez et al. |
| 2021/0145433 A1 | 5/2021 | Sengun et al. |
| 2021/0282763 A1 | 9/2021 | Sengun et al. |
| 2022/0167959 A1 | 6/2022 | Sengun |
| 2022/0296229 A1 | 9/2022 | Sengun |
| 2023/0112112 A1 | 4/2023 | Sengun |
| 2023/0135885 A1 | 5/2023 | Snyder et al. |
| 2023/0210517 A1 | 7/2023 | Sengun |

FOREIGN PATENT DOCUMENTS

| | | |
|---|---|---|
| CA | 2772500 C | 4/2018 |
| CN | 2719234 Y | 8/2005 |
| CN | 101252887 A | 8/2008 |
| CN | 101961256 A | 2/2011 |
| CN | 101442944 B | 6/2011 |
| CN | 101961257 B | 10/2015 |
| CN | 102113901 B | 8/2016 |
| CN | 102551824 B | 9/2016 |
| EP | 0706779 B1 | 5/2000 |
| EP | 0870471 B1 | 6/2003 |
| EP | 1568326 B1 | 10/2007 |
| EP | 1199035 B1 | 2/2008 |
| EP | 1707127 B1 | 12/2010 |
| EP | 2572650 A1 | 3/2013 |
| EP | 2662032 B1 | 10/2015 |
| EP | 2455004 B1 | 12/2016 |
| EP | 2277457 B1 | 1/2019 |
| EP | 2455003 B1 | 6/2021 |
| JP | S6290148 A | 4/1987 |
| JP | H067422 A | 1/1994 |
| JP | H08206122 A | 8/1996 |
| JP | 2000512193 A | 9/2000 |
| JP | 2003528648 A | 9/2003 |
| JP | 2005237966 A | 9/2005 |
| JP | 2006516468 A | 7/2006 |
| JP | 2007075616 A | 3/2007 |
| JP | 2008514382 A | 5/2008 |
| JP | 2008543509 A | 12/2008 |
| JP | 2009522065 A | 6/2009 |
| JP | 2010521195 A | 6/2010 |
| JP | 2011025034 A | 2/2011 |
| JP | 2012110711 A | 6/2012 |
| JP | 2012110712 A | 6/2012 |
| WO | 1995019139 A1 | 7/1995 |
| WO | 1997017901 A1 | 5/1997 |
| WO | 1998011825 A1 | 3/1998 |
| WO | 1998042261 A1 | 10/1998 |
| WO | 2001006933 A2 | 2/2001 |
| WO | 2003022161 A1 | 3/2003 |
| WO | 2007002561 A1 | 1/2007 |
| WO | 2007005394 A1 | 1/2007 |
| WO | 2007078281 A2 | 7/2007 |
| WO | 2007109769 A1 | 9/2007 |
| WO | 2009107121 A2 | 9/2009 |
| WO | 2010028324 A2 | 3/2010 |
| WO | 2010105046 A1 | 9/2010 |

OTHER PUBLICATIONS

End Definition Meaning & Dictionary.com, https://www.dictionary.com/browse/end accessed Nov. 23, 2024 (Year 2024).

[No Author Listed] Arthex is Reaching New Heights In Rotar Cuff Repair. Arthex Inc. 2007. 8 pages.

[No Author Listed] Arthroscopic Knot Tying Manual 2005. DePuy Mitek. 27 pages.

[No Author Listed] Gryphon Brochure. DePuy Mitek. 2 pages (undated).

[No Author Listed] Versalok Anchor. Brochure. DePuy Mitek, a Johnson & Johnson company, 92 pp. 2007.

Adjacent Definition & Meaning, https://www.dictionary.com/browse/adjacent, copyright 2022 Dictionary.com, LLC (Year: 2022).

(56) References Cited

OTHER PUBLICATIONS

Allcock, The Encyclopedia of Polymer Science, vol. 13, pp. 31-41, Wiley Intersciences, John Wiley & Sons, 1988.
Anchor Definition & Meaning, Merriam-Webster, https://www.merriam-webster.com/dictionary/anchor; copyright 2022 Merriam-Webster, Incorporated (Year: 2022).
Chinese Office Action for Application No. 201310163420.7, issued May 5, 2016 (21 pages).
Chinese Office Action for Application No. 201310163700.8 issued Jun. 3, 2016 (14 pages).
Chinese Office Action for Application No. 201310429109.2 issued Oct. 24, 2016 (13 pages).
Chinese Office Action for Application No. 201310741440.8, issued Jan. 26, 2017 (12 pages).
Cohn et al., Biodegradable PEO/PLA block copolymers. J Biomed Mater Res. Nov. 1988;22(11):993-1009.
Cohn et al., Polym Preprint. 1989;30(1):498.
Dahl et al., Biomechanical characteristics of 9 arthroscopic knots. Arthroscopy. Jun. 2010;26(6):813-8.
EP Search Report for Application No. 11190157.5 issued Feb. 27, 2012. (8 pages).
Extended European Search Report for Application No. 11190157.5 issued Jul. 6, 2012. (10 pages).
EP Search Report for Application No. 11190159.1 issued Feb. 21, 2012. (8 pages).
Extended European Search Report for Application No. 11190159.1 issued Jul. 6, 2012. (11 pages).
Extended European Search Report for Application No. 11195100.0 issued Oct. 17, 2012. (7 pages).
Extended European Search Report for Application No. 13166905.3 issued Aug. 13, 2013 (9 pages).
Extended European Search Report for Application No. 13166907.9, issued Aug. 1, 2013 (6 pages).
Extended European Search Report for Application No. 13166908.7, issued Aug. 23, 2013 (8 pages).
Extended European Search Report for Application No. 13185425.9 issued Dec. 16, 2013 (9 pages).
Extended European Search Report for Application No. 13199724.9 issued Apr. 4, 2014 (6 pages).
Extended European Search Report for Application No. 16205548.7, issued Dec. 22, 2017 (11 pages).
Extended European Search Report for Application No. 21178549.0, issued Nov. 17, 2021 (22 pages).
Extended European Search Report for Application No. 21178459.0, issued Nov. 17, 2021 (22 pages).
Google dictionary definition of the term "Tube" retrieved Nov. 24, 2019 (Year: 2019).
Heller, Handbook of Biodegradable Polymers, edited by Domb, et al., Hardwood Academic Press, pp. 99-118 (1997).
Indian First Examination Report for Application No. 3243/DEL/2011, issued Dec. 30, 2019 (6 pages).
International Search Report for Application No. PCT/US2011/067119, mailed Jun. 4, 2012. (6 pages).
Japanese Office Action for Application No. 2011-281088, issued Nov. 10, 2015 (4 pages).
Japanese Office Action for Application No. 2013546447, issued Nov. 17, 2015 (3 pages).
Japanese Office Action for Application No. 2013-097645, mailed May 9, 2017 (6 pages).
Japanese Office Action for Application No. 2013-268840, mailed Sep. 26, 2017 (5 pages).
Kemnitzer et al., Handbook of biodegradable Polymers. Eds. Domb et al. Hardwood Acad. Press. 1997;251-72.
Vandorpe et al., Handbook of Biodegradable Polymers, edited by Domb, et al., Hardwood Acad. Press, pp. 161-182 (1997).

\* cited by examiner

SURGICAL CONSTRUCTS WITH COLLAPSING SUTURE LOOP AND METHODS FOR SECURING TISSUE

PRIORITY

The present application is a continuation of and claims priority to U.S. patent application Ser. No. 16/826,432, filed Mar. 23, 2020, and entitled "Surgical Constructs with Collapsing Suture Loop and Methods for Securing Tissue," which is a continuation of and claims priority to U.S. patent application Ser. No. 15/648,068, filed Jul. 12, 2017, and entitled "Surgical Constructs with Collapsing Suture Loop and Methods for Securing Tissue," and which issued as U.S. Pat. No. 10,631,848 on Apr. 28, 2020, which is a divisional of and claims priority to U.S. patent application Ser. No. 14/145,486, filed Dec. 31, 2013, and entitled "Surgical Constructs with Collapsing Suture Loop and Methods for Securing Tissue," and which issued as U.S. Pat. No. 9,737,293 on Aug. 22, 2017, which claims priority to and the benefit of U.S. Provisional Application No. 61/791,079, filed on Mar. 15, 2013, and entitled "Suture Anchor System with Collapsing Suture Loop," the contents of each of which is hereby incorporated by reference in their entireties.

FIELD

The present disclosure relates to surgical constructs and methods for securing soft tissue to bone, and more particularly relates to surgical constructs having a collapsing suture loop.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to soft and weak bones leading to inadequate fixation between the anchor and bones and the anchors and filaments with which the anchors are coupled.

Repair constructs made from one or more surgical filaments are typically used in soft tissue repair procedures to secure the tissue in a desired location. The repair constructs are typically disposed through one or more portions of the tissue to be repaired, which can cause trauma to the tissue, and are often coupled to anchors disposed in bone to which the tissue is to be approximated. While devices and techniques have been developed to help minimize trauma associated with passing repair constructs through tissue, there is still room for further improvement. For example, some repair constructs may include a sleeve disposed around at least a portion of the limbs of filament of the construct. The sleeve can assist in minimizing trauma to tissue, and also in managing the limbs of suture while the construct is being disposed through tissue. However, the sleeve still adds extra size above and beyond the thickness of the suture, and thus can be a source for added trauma to the tissue. Sleeves also add further costs to the constructs.

In other instances, sutures used in repairs can have portions that have a thicker profile, for instance because they have extra loops, knots, or other configurations formed therein as part of the construct. Thicker profiles can, not surprisingly, provide additional sources of trauma for the tissue as these portions of the construct pass through the tissue. As a result, procedures can often include extra steps to avoid passing portions of the construct that have thicker profiles through tissue. For example, in some instances, a shuttle suture is used to pull the construct through tissue so that an end with a thicker profile does not have to be passed through tissue. The use of additional components, such as a shuttle suture, however, can be cumbersome. Further, to generally avoid trauma to tissue, some procedures may only involving passing a construct through tissue one time. This approach, however, can lead to unsecure tissue attachments due to the footprint of the construct holding the tissue not being large enough.

Still further, there remains a desire to minimize the number of knots used in conjunction with the repair construct when performing soft tissue repair procedures. A variety of different knots, such as sliding knots, can be used to help draw and secure soft tissue with respect to bone. Although the tying of knots at a surgical site is common, in some instances knots can have a tendency to slip, which in turn can cause a loss of tension between the tissue and bone. This drawback is sometimes referred to as a loss of "loop security." In addition to this "loop security" issue, conventional knots typically have an overall size that can be obstructive or intrusive, especially in tight joints, which may damage cartilage or other tissue by abrasion with the knot.

It is therefore desirable to provide repair constructs and methods that reduce the amount of trauma associated with using repair constructs while maintaining or improving the holding strength such constructs and methods can provide. It is also desirable to provide surgical repair methods that reduce the number of steps performed without losing the integrity of the repair performed. Further, it is desirable to provide constructs and methods for use in soft tissue repair that minimize or eliminate the number and size of knots to be tied by a surgeon, particularly during arthroscopic repair procedures.

SUMMARY

Surgical constructs and methods are generally provided for securing soft tissue to bone. In one exemplary embodiment, the surgical construct is formed from a suture filament and includes a first terminal end of the filament, a second terminal end of the filament, and an intermediate portion of the filament disposed along at least a portion of a length extending between the first and second terminal ends. The construct can further include a coaxial region formed by the first terminal end being disposed within a volume of a portion of the intermediate portion, and a continuous, closed loop extending from a first side of the coaxial region. The loop can have a first end that is directly adjacent to the first side of the coaxial region, and a second, opposed end formed by a fold in the suture filament. The second, opposed end of the loop can be a first terminal end of the construct, while the second terminal of the filament can extend from a second side of the coaxial region and be a second terminal end of the construct.

A length of the loop of the construct can be configured to be adjusted by moving the first terminal end of the filament with respect to the coaxial region. The construct itself can have a variety of configurations and sizes. By way of non-limiting examples, in some embodiments a length of the coaxial region can be at least about 15.24 centimeters.

Likewise, in some embodiments a length of the loop can be at least about 20.32 centimeters. A pick count of the coaxial region can be in a range of about 30 picks per 2.54 centimeters to about 60 picks per 2.54 centimeters. In one exemplary embodiment the pick count of the coaxial region is approximately 40 picks per 2.54 centimeters. In some embodiments, the construct can include an anchor having a filament engagement feature at a distal end thereof. The suture filament can engage th filament engagement feature such that the first terminal end of the construct extends from one side of the filament engagement feature and the second terminal end of the construct extends from an opposite side of the filament engagement feature.

One exemplary embodiment of a surgical repair method includes inserting an anchor in bone and in proximity to detached soft tissue. The anchor can have a surgical filament associated therewith, with the filament having a first portion with a loop formed therein, a second portion that includes a terminal end, and a coaxial region formed between the first and second portions by disposing a portion of the filament into its own volume. The method can include passing the terminal end of the second portion of the filament through a portion of the detached soft tissue, forming a snare in the loop of the first portion of the filament after the anchor has been inserted in bone in proximity to detached soft tissue, and passing the terminal end of the second portion through the snare. The snare can be collapsed to engage the soft tissue and advanced distally to bring the tissue into proximity with the bone. The coaxial region can be deconstructed by removing the portion of the filament from the volume of the filament in which it was disposed.

Another step that can be provided as part of the method includes passing the loop through a portion of the detached soft tissue before forming the snare in the loop. Further, in some instances the method can include tying at least one locking knot with the filament at a location that is proximate to the collapsed snare to secure a location of the filament with respect to the tissue.

In some embodiments the anchor can have a second surgical filament associated with it. The second filament can include a first portion with a loop formed therefrom, a second portion that includes a terminal end, and a coaxial region formed between the first and second portions by disposing a portion of the filament into its own volume. In such an embodiment, the method can further include passing the terminal end of the second portion of the second filament through a portion of the detached soft tissue and passing the loop of the second filament through a portion of the detached soft tissue. After the loop has been passed through the tissue, a snare can be formed in that loop. The terminal end of the second portion of the second filament can be passed through the snare of the second filament, the snare can be collapsed to engage the soft tissue, and then the collapsed snare can be advanced distally to bring the tissue into proximity with the bone. The coaxial region of the second filament can be deconstructed by removing the portion of the second filament from the volume of the second filament in which it was disposed. Deconstructing the coaxial regions of the first and second filaments can result in a first limb and a second limb extending from their respective collapsed snares. The first and second limbs of both filaments can then be attached to a second anchor, and tension can be applied to the limbs to secure a location of the same with respect to the second anchor. For example, tension can be applied by inserting the second anchor into bone with the first and second limbs being disposed between an outer wall of the anchor and the bone. In some embodiments, the locations of the first and second limbs of the filaments with respect to the second anchor can be secured without tying a knot in either of the first or second filaments.

In another embodiment in which a second surgical filament is provided, the filament can have a first portion with a snare formed therein, a second portion that includes a terminal end, and a coaxial region formed between the first and second portions by disposing a portion of the filament into its own volume. The snare in the first portion can be pre-existing, or alternatively, it can be formed in the construct at some point during the procedure. In addition to using the first filament as described earlier, the method can further include passing the terminal end of the second portion of the second filament through a portion of the detached soft tissue and passing the first portion of the second filament through an opening extending through a length of the anchor. The terminal end of the second filament can be passed through the snare of the second filament, the snare can be collapsed to engage the soft tissue, and then the collapsed snare can be advanced distally to bring the tissue into proximity with the bone. As a result, the first filament can be disposed between the collapsed snare of the second filament and the soft tissue.

Another exemplary embodiment of a surgical repair method includes inserting an anchor in bone in proximity to detached soft tissue. The anchor can have a surgical construct associated therewith, with the construct having a first terminal end and a second terminal end. The method can include passing the first terminal end through a portion of the detached soft tissue, passing the second terminal end through a portion of the detached soft tissue, and then subsequently forming a Lark's Head cinch loop in the second terminal end of the surgical construct such that the Lark's Head cinch loop defines a receiving opening. The first terminal end of the construct can be passed through the receiving opening, the receiving opening can be collapsed, and the collapsed Lark's Head cinch loop can be advanced distally to bring the tissue into proximity with the bone.

The surgical construct can be formed from a surgical filament having a first terminal end, a second terminal end, and an intermediate portion extending therebetween, with the first terminal end of the construct being the first terminal end of the filament, and the second terminal end of the construct having a loop formed by the second terminal end of the filament being disposed in a portion of the intermediate portion of the filament. The method can further include removing the second terminal end of the filament from the intermediate portion of the filament after collapsing the receiving opening of the Lark's Head cinch loop, and tying at least one knot with the filament at a location that is proximate to the collapsed Lark's Head cinch loop to secure a location of the filament with respect to the tissue.

In some embodiments, the anchor can have a second surgical construct associated therewith. The second construct can be formed from a second surgical filament having a first terminal end, a second terminal end, and an intermediate portion extending therebetween. A first terminal end of the second construct can be the first terminal end of the second filament, and a second terminal end of the second construct can have a loop formed by the second terminal end of the second filament being disposed in a portion of the intermediate portion of the second filament. In addition to using the first construct as described earlier, the method can further include passing the terminal end of the second construct through a portion of the detached soft t issue and passing the second terminal end of the second construct through a portion of the detached soft tissue. After the first and second terminal ends of the second construct have been passed through portions of the detached tissue, a Lark's Head cinch loop can be formed in the second terminal end of the second construct, with the knot defining a receiving opening. The first terminal end of the second construct can be passed through the receiving opening of the second construct, the opening can be collapsed, and then the collapsed Lark's Head cinch loop can be advanced distally to bring the tissue into proximity with the bone. After collapsing the receiving opening of the Lark's Head cinch loop, the method can further include removing the second terminal end of the first filament from the intermediate portion of the first filament and removing the second terminal end of the second filament from the intermediate portion of the second filament to provide first and second limbs of each of the first and second filaments extending from the respective collapsed Lark's Head cinch loops. The first and second limbs of both filaments can then be attached to a second anchor, and tension can be applied to the limbs to secure a location of the same with respect to the second anchor. For example, tension can be applied by inserting the second anchor into bone with the first and second limbs being disposed between an outer wall of the anchor and the bone. In some embodiments, the locations of the first and second limbs of the filaments with respect to the second anchor can be secured without tying a knot in either of the first or second filaments.

In another embodiment in which a second surgical construct is associated with the anchor, the construct can include a first terminal end and a second terminal end, the second terminal end having a snare formed therein. The snare in the second terminal end can be pre-existing, or alternatively, it can be formed in the construct at some point during the procedure. In addition to using the first construct as described earlier, the method can further include passing the first terminal end of the second construct through a portion of the detached tissue and passing the second terminal end of the second construct through an opening extending through a length of the anchor. The first terminal end of the second construct can be passed through the snare of the second construct, the snare can be collapsed, and then the collapsed snare can be advanced distally to bring the tissue into proximity with the bone. As a result, the first construct can be disposed between the collapsed snare of the second construct and the soft tissue.

BRIEF DESCRIPTION OF DRAWINGS

This invention will be more fully understood from the following detailed description taken in conjunction with the accompanying drawings, in which.

DETAILED DESCRIPTION

Figure 1A:
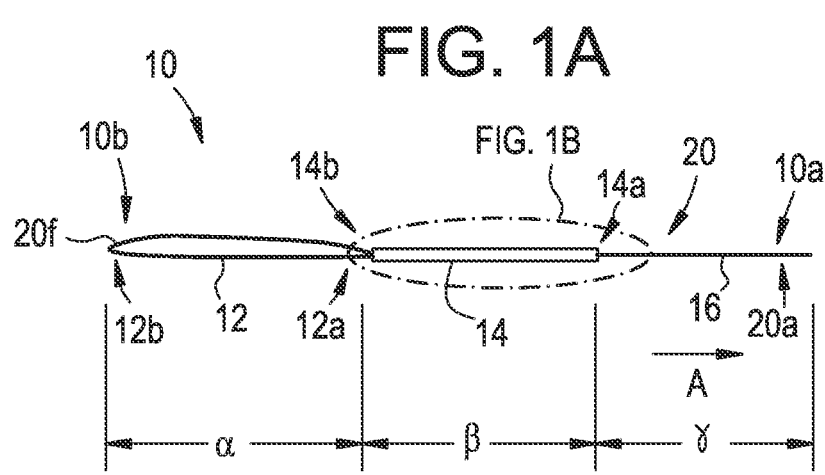
FIG. 1A is a schematic view of one exemplary embodiment of a surgical repair construct formed from a suture filament.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Additionally, to the extent that linear or circular dimensions are used in the description of the disclosed constructs and methods, such dimensions are not intended to limit the types of shapes that can be used in conjunction with such constructs and methods. A person skilled in the art will recognize that an equivalent to such linear and circular dimensions can easily be determined for any geometric shape. Sizes and shapes of the constructs, and the components thereof, can depend at least on the anatomy of the subject in which the constructs will be used, the size and shape of components with which the constructs will be used, and the methods and procedures in which the constructs will be used.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. Additionally, although terms such as "first" and "second" are used to describe various aspects of a component, e.g., a first end and a second end, such use is not indicative that one component comes before the other. Use of terms of this nature may be used to distinguish two similar components or features, and often such first and second components can be used interchangeably. Still further, a number of terms may be used throughout the disclosure interchangeably but will be understood by a person skilled in the art. By way of non-limiting example, the terms "suture" and "filament" may be used interchangeably.

Surgical repair constructs and methods for soft tissue repair are generally provided and they generally involve the use of surgical filaments that are configured in a variety of manners to minimize and/or eliminate the tying of knots during a surgical procedure while also minimizing the amount of trauma imparted by the constructs to tissue with which the constructs are used. The constructs described herein provide superior strength for use in a number of different surgical procedures, such as rotator cuff and instability repair procedures and other types of tendon and tissue repair procedures. The designs of the constructs described herein are such that they have a particularly low profile, thereby allowing both terminal ends of a construct to pass through the tissue with minimal trauma to the tissue and to become associated with the tissue without tying knots. The low profile results from inserting one limb of filament into another and eliminating any sort of sleeve, which is often used to assist in shuttling limbs of filament through tissue. The ability to pass both terminal ends of the construct through tissue with minimal trauma to the tissue results from the aforementioned low profile configuration and because the disclosed constructs are generally configured to have one terminal end that is a single filament and a second terminal end that is a loop in which opposed portions of the loop each are formed of a single filament. Passing a single filament, or two single filaments as part of a loop, through tissue results in minimal trauma to the tissue.

Figure 1B:
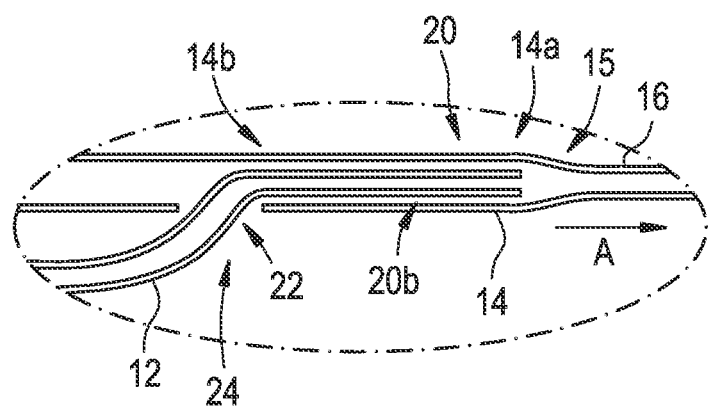
FIG. 1B is a detail view of a coaxial region of the surgical repair construct of FIG. 1A.

As shown by one exemplary embodiment of a surgical repair construct 10 in FIG. 1A, the construct 10 can generally be formed from a single elongate filament 20, which is used in the formation of three distinct portions of the construct 10: a loop 12, a coaxial region 14, and a tail 16. The filament 20 includes two terminal ends 20a, 20b with an intermediate portion extending therebetween. The first terminal end 20a can also be a terminal end 10a of the construct 10. Thus, as shown, the first terminal end 20a is part of the tail 16. The second terminal end 20b, which is illustrated in FIG. 1B, can be part of the coaxial region 14 formed in an intermediate portion of the construct 10. More particularly, as shown, the second terminal end 20b passes through an opening 22 of an outer surface of the intermediate portion of the filament 20 to form a loop closure 24, and then extends into a volume of the filament 20. The opening 22 can be manually formed in the filament 20, for instance by puncturing it, or it can be an opening that forms as part of a braided configuration.

At least a portion of the volume of the filament 20 can be hollow to receive the terminal end 20b. In some instances, the entire volume of the filament 20 can be hollow. This can be achieved, for example by removing a core from the entire length of the filament 20 using techniques known to those skilled in the art. In other embodiments, only a portion of the core is removed, such as the portion in which the terminal end 20b will be disposed. Still further, in other embodiments no core may be removed such that the second terminal end 20b and the core are both disposed within the volume of the filament 20. Alternatively, or in addition to, in instances in which the filament 20 is a braided filament, the portion of the filament 20 configured to be the volume that receives the terminal end 20b to form the coaxial region 14 can have a reduced pick count. Reducing the pick count can provide for additional flexibility, and thus additional volume, to receive the terminal end 20b.

The loop closure 24 can be a self-maintaining junction. As a result, pulling on the tail 16 does not cause the terminal end 20b to pull out of the volume of the filament 20 in which it is disposed. Rather, pulling on the tail 16 can actually force the volume of the filament 20 to collapse around the terminal end 20b, thereby providing sufficient friction between the terminal end 20b and the filament 20 to hold them together. The terminal end 20b, however, can be removed from the volume manually at the opening 22 by applying a sufficient amount of force.

Although in the illustrated embodiment the loop closure 24 is formed by inserting the second terminal end 20b into a volume of the filament 20, a person skilled in the art will understand other ways by which this junction can be formed without departing from the spirit of the present disclosure. By way of non-limiting examples, the terminal end 20b can be adhered to the filament 20, passed from one side of the filament 20 through to the other side, or it can be wrapped around the filament 20 and held in place by one or more features known to those skilled in the art. For instance, a removable pin or flexible member can be passed across the terminal end 20b and a portion of the filament 20 that serves as the coaxial region 14 to maintain the location of the terminal end 20b with respect to other portion of the filament 20. When the pin is removed, the terminal end 20b can then be moved with respect to the portion of the filament 20 that serves as the coaxial region 14. Additional disclosures related to such a pin or flexible member are provided in U.S. Patent Application Publication No. 2013/0296931, the content of which is incorporated herein by reference in its entirety.

The second terminal end 20b is not only a part of the coaxial region, but it also helps define a length α of the loop 12. The loop 12 can be a continuous, closed loop configured to have an adjustable length. More particularly, the second terminal end 20b can be configured to move with respect to the volume in which it is disposed to adjust the length α of the loop 12. As shown in FIG. 1A, the loop 12 is generally defined as having a first end 12a that is directly adjacent to a second side 14b of the coaxial region 14 and a second end 12b that is formed by a fold 20f in the suture filament 20, the second end 12b also doubling as the terminal end 10b of the construct 10. The continuous, closed loop 12 can be adjustable such that moving the terminal end 20b with respect to the volume in which it is disposed can change the length α of the loop 12. As shown, applying a force in a direction A can decrease a length α of the loop 12, and moving the second terminal end 20b out of the opening 22 can increase the length α of the loop 12. As described herein, the loop 12 can have a small profile allowing it to be easily passed through tissue while causing a minimal amount of trauma to the tissue.

A first side 14a of the coaxial region can have the tail 16 extending therefrom. The tail 16 can extend away from the coaxial region 14 and can be used in conjunction with the loop 12 to help both draw soft tissue towards bone and subsequently maintain the location of the tissue with respect to the bone. As shown in FIG. 1B, a transition 15 between the second side 14b and the tail 16 is smooth once the terminal end 20b is not disposed any further in the volume of the filament 20. The thickness of the filament 20 becomes reduced due to the fact that no other portion of the filament is disposed in the tail 16. The smooth nature of the transition 15 makes it easier to pass the filament 20 through tissue.

The construct 10 configuration illustrated in FIGS. 1A and 1B provides a number of benefits, at least due in part to the second terminal end 20b being disposed in a volume of an intermediate portion of the filament 20. For example, the configuration helps with suture management because by disposing an end of the filament within another portion of the filament, it is one fewer end for which a surgeon needs to account. This is particularly useful in embodiments in which multiple constructs are disposed on a single anchor, as described further below, because each construct has multiple ends for which to account. The disclosed configuration essentially halves the number of filament ends to manage. The configuration also helps prevent filament tangling. The terminal end 20b cannot tangle with other portions of the filament 20, or other components being used as part of a procedure, when it is disposed within the volume of the filament 20. A further benefit that results from the configuration is that it affords surgeons better visibility. There are fewer filaments ends that can be in the surgeon's field of view when the terminal end 20b is disposed within the volume of the filament 20. Still further, because no additional components are used to help achieve these benefits, this configuration provides a cheap and easy way to pass filaments through tissue, while also taking up a minimal amount of space.

The filament 20 used to form the construct 10 can be any type and material typically used as filament, including a cannulated filament, a braided filament, and a mono filament. The type and strength of the filament can depend, at least in part, on the other components with which the construct is used, such as an anchor, the tissue through which it will be passed or coupled to, and the type of procedure in which it is used. In some embodiments the filament can have a size between about a #5 filament (about 20 gauge to about 21 gauge) and about a #5-0 filament (about 35 gauge to about 38 gauge), and in one exemplary embodiment the filament is a #2 filament (about 22 gauge to about 24 gauge), such as an Orthocord™ filament that is commercially available from DePuy Mitek, Inc., DePuy Mitek Inc., 325 Paramount Drive, Raynham, Massachusetts 02767, or an Ethibond™ filament that is commercially available from Ethicon, Inc., Route 22 West, Somerville, NJ 08876.

The thickness of the filament should provide strength in the connection but at the same time minimize the trauma caused to tissue through which it passes. In some embodiment, different portions of the construct 10 can have different thicknesses, with the thickness being based, at least in part, on the purpose for that portion, the thicknesses of the other portions of the construct, the components or tissue through which that portion may be passed, and the type of procedure in which the construct is used. Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed.

The lengths of the various portions of the construct 10 can likewise depend, at least in part, on the other components with which the construct is used, the tissue through which it will be passed or coupled to, the lengths of the various portions of the construct, and the type of procedure in which the construct is used. As illustrated in FIG. 1A, a length α of the loop 12 can be in the range of about 12.7 centimeters to about 50.8 centimeters, a length β of the coaxial region 14 can be in the range of about 7.62 centimeters to about 50.8 centimeters, and a length γ of the tail 16 can be in the range of about 12.7 centimeters to about 101.6 centimeters, and in one embodiment the length α of the loop 12 is approximately 21.59 centimeters, a length β of the coaxial region 14 is approximately 21.59 centimeters, and a length γ of the tail 16 can be about 25.4 centimeters. There is no specific ratio for any of lengths α, β, and γ, and thus in other embodiments the lengths α and β can be different, and one or both of lengths α and β can be larger than length γ. It can be desirable for the length α of the loop 12 to be long enough so that it can be disposed outside of a cannula when in use, as described in greater detail below. This makes it easier for the surgeon to work with the construct 10, and to monitor it to insure no undesirable tangling of portions of the filament 20 occurs. For example, in some embodiments, the length α of the loop 12 can be at least about 20.32 centimeters, or at least about 21.59 centimeters, or even longer. Similarly, it can be desirable for the length β of the coaxial region 14 to be long enough so that the terminal end 20b does not fall out of the volume of the filament 20, and long enough so that when the coaxial region is disassembled, as described in greater detail below, the two limbs that result from the disassociation are long enough to be grasped by a surgeon outside of the cannulas. For example, in some embodiments, the length β of the coaxial region 14 can be at least about 7.62 centimeters, at least about 15.24 centimeters, at least about 20.32 centimeters, or even longer. A length of the filament 20 itself can be in the range of about 38.1 centimeters to about 203.2 centimeters, and in one exemplary embodiment it has a length of about 111.76 centimeters.

In embodiments in which the filament 20 is braided, the pick count of the braid can be adjusted to assist in receiving the terminal end 20b. For example, the pick count for a portion of the filament 20 configured to receive the terminal end 20b to form the coaxial region 14 can be approximately in the range of about 30 picks per 2.54 centimeters to about 60 picks per 2.54 centimeters, and in one instance the pick count can be about 40 picks per 2.54 centimeters. A person skilled in the art will recognize that other pick counts can be used depending, at least in part, on the size of the terminal end 20b to be received, the type of tissue through which the coaxial region 14 will be disposed, and the various desired properties of the overall construct, such as the ease of sliding a filament within the volume of the filament 20.

Figure 2:
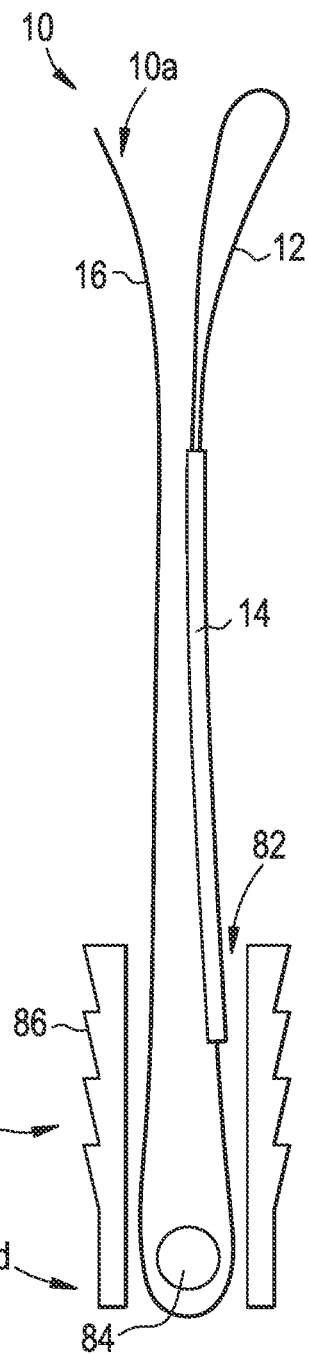
FIG. 2 is a schematic view of the surgical repair construct of FIG. 1A coupled to a suture anchor.

As shown in FIG. 2, the construct 10 can be coupled to a suture anchor 80. The suture anchor 80 can have an internal cannulation 82 extending through a portion thereof and one or more filament engagement features, such as the filament engagement feature 84 disposed at a distal end 80d of the anchor 80. In the illustrated embodiment, the loop 12 extends from one side of the anchor 80 and the terminal end 10a, including at least a portion of the tail 16, extends from the other side of the anchor 80. Although in the illustrated embodiment the coaxial region is disposed on the same side as the loop 12, in other embodiments the coaxial region 14 can be at least partially disposed on the same side as the terminal end 10a, at least because the construct 10 can generally be configured to slide with respect to the filament engagement feature 84 to move to various locations with respect to the anchor 80. The anchor can also include one or more external fixation enhancements, such as threads 86, for engaging bone in which the anchor can be disposed.

One skilled in the art will appreciate that a variety of suture anchor types can be used in conjunction with the constructs provided herein, including both hard and soft anchors, and that the disclosure is not intended to be limited to the designs of anchors provided for herein. Some exemplary embodiments of anchors that can be used in conjunction with the constructs and related teachings provided for herein include a Healix Ti™ anchor, a Healix Advance™ anchor, a Healix Advance™ Knotless anchor, a Versalok™ anchor, and a Gryphon™ anchor, each of which is commercially available from DePuy Mitek, Inc., as well as anchors described in U.S. Patent Application Publication No. 2013/0296934, and U.S. patent application Ser. No. 13/623,429, entitled "Systems, Devices, and Methods for Securing Tissue Using Hard Anchors," filed Sep. 20, 2012, the content of which is incorporated by reference herein in their entireties.

Figure 3A:
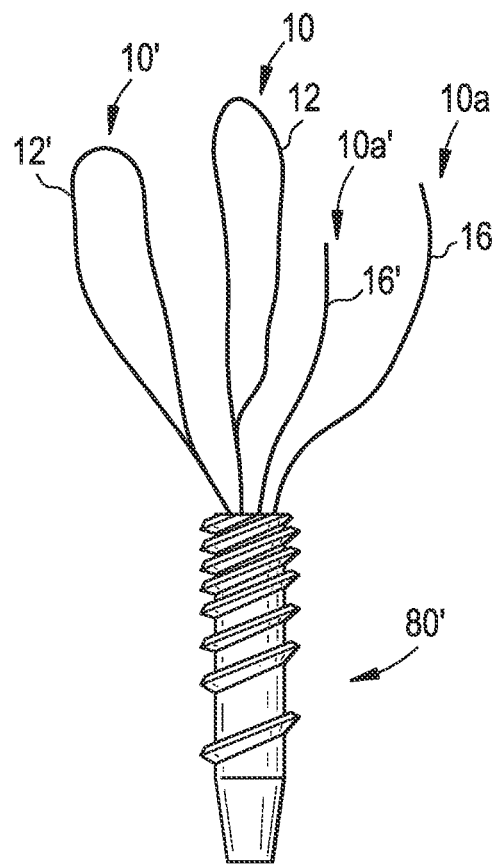
FIG. 3A is a schematic view of another exemplary embodiment of a surgical repair construct, the construct being formed from two separate suture filaments, each filament having the configuration of the filament of the repair construct of FIG. 1A, and each filament being coupled to a suture anchor.
Figure 3B:
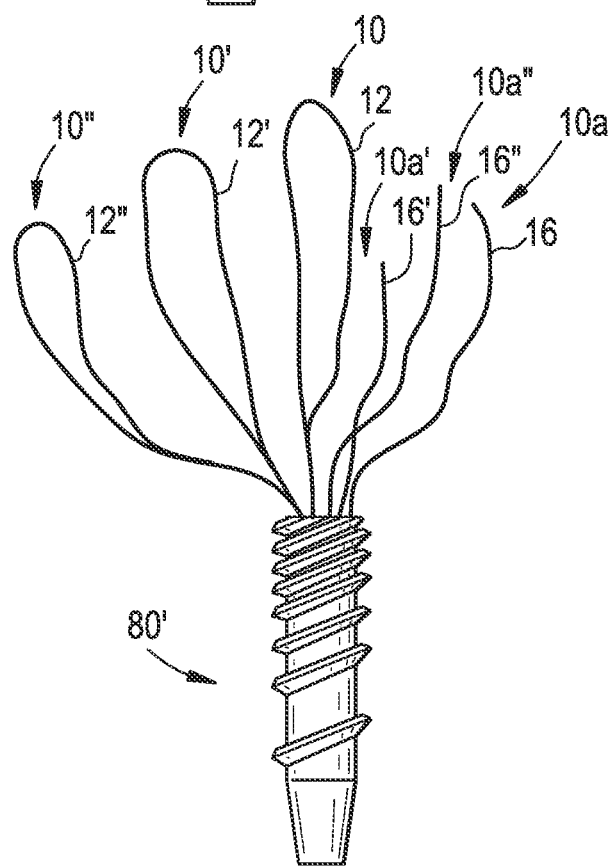
FIG. 3B is a schematic view of still another exemplary embodiment of a surgical repair construct, the construct being formed from three separate suture filaments, each filament having the configuration of the filament of the repair construct of FIG. 1A, and each filament being coupled to the suture anchor of FIG. 3A.

While FIG. 2 illustrates a single construct associated with the anchor 80, in other embodiments more than one construct can be loaded onto the anchor 80. By way of non-limiting examples, FIG. 3A illustrates an embodiment in which constructs 10, 10' are double-loaded onto a suture anchor 80', and FIG. 3B illustrates an embodiment in which constructs 10, 10', 10" are triple-loaded onto the suture anchor 80'. The suture anchor 80' can include a filament engagement feature (not shown) around which each construct 10, 10', 10" can be disposed. As a result, the loops 12, 12', and 12" can be disposed on one side of the anchor 80' and the terminal ends 10a, 10a', and 10a" including at least a portion of the tails 16, 16', and 16" can be disposed on an other side of the anchor 80'.

Each construct 10, 10', 10" disposed around the filament engagement feature can be in a touching, side-by-side disposition. In other embodiments one construct can be disposed over a portion of another as they wrap around a portion of the filament engagement feature. The use of multiple constructs with one anchor can increase the resulting footprint of the implant. Further, as the number of constructs associated with the anchor 80' increases, the benefits of the provided for configurations are magnified. In particular, the suture management benefits are even more pronounced with two and three constructs associated with the anchor 80' than with one construct. As the number of constructs increase, the size of the constructs can remain the same, or they can decrease to help allow more filaments to be attached to the anchor and used without interfering with the other filaments. By way of non-limiting example, in some exemplary embodiments of a single construct or two constructs being associated with an anchor the filament forming the construct(s) can be a #2 (about 22 gauge to about 24 gauge) Orthocord™ filament, and in some exemplary embodiments of three constructs being associated with an anchor the filament forming the three constructs can be a #0 (about 26 gauge to about 27 gauge) Orthocord™ filament.

The use of multiple constructs can also enhance the type and effectiveness of various tissue repair surgical procedures, including those discussed below and others known to those skilled in the art. Each construct can have a unique identifier to assist the surgeon in identifying a particular filament during the procedure. Examples of unique identifiers include, but are not limited to, different colors, patterns, or surfaces to provide different tactile feels. Additionally, each construct 10 itself can have unique identifiers associated with each terminal end, thus making it easier for a surgeon to know which end has the loop 12 and which is the tail 16. Identifying the two different ends of a single construct can be helpful in allowing the surgeon to know which end will serve as a post along which a collapsed Lark's Head cinch loop is distally advanced, as described in greater detail below.

The size of the anchor 80' can depend on a variety of factors, including, by way of non-limiting example, the type and size of the constructs with which it is used, the bone in which it will be disposed, and the type of procedure in which it will be used, but in some exemplary embodiments it can have an outer diameter in the range of about 3 millimeters to about 6 millimeters, and in one embodiment its outer diameter can be about 4.75 millimeters. Further, although in the illustrated embodiments the constructs 10, 10', and 10" are associated with an anchor 80', other types of implantation devices can also be used in conjunction with the constructs 10, 10', and 10". Such devices include, by way of non-limiting example, cortical buttons and other strands of suture filament. Alternatively, the construct 10 can be used independent of an anchor, for instance to help grasp or tie tissue and the like, as described further below and in greater detail in U.S. Patent Application Publication No. 2013/0296931, the content of which was previously incorporated herein by reference.

Figure 4A:
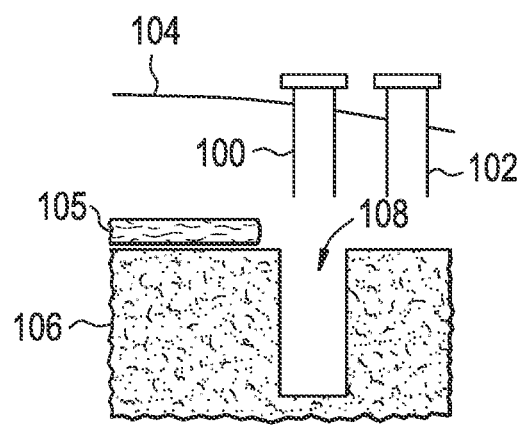
FIGS. 4A-4N are sequential, schematic, cross-sectional views of one exemplary embodiment for using the surgical repair construct of FIG. 2 to secure tissue to bone.
Figure 4B:
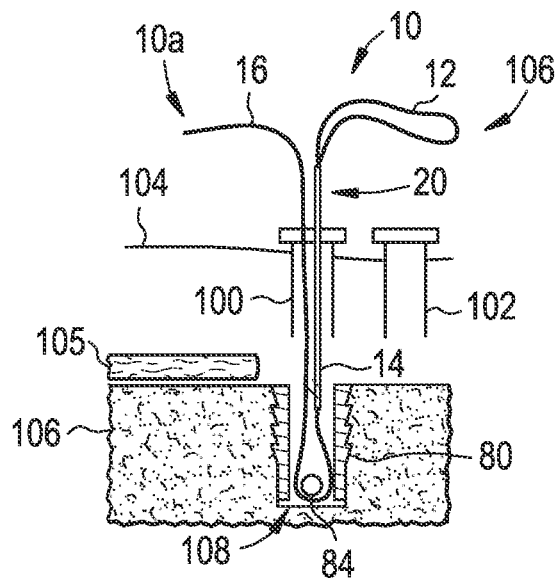

Exemplary methods for using constructs of the type described herein are now described in further detail. The methods described herein generally relate to attaching soft tissue, such as tendon 105, to bone, although a person skilled in the art will recognize other types of procedures with which the constructs and the methods related to the same can be used. The embodiment illustrated in FIGS. 4A-4N is performed in a minimally invasive manner, e.g., arthroscopically, through a first cannula 100 and a second cannula 102 that are disposed through a patient's skin 104 using techniques known to those skilled in the art. The use of multiple cannulas can help a surgeon manage filament during a surgical procedure, as well as any instruments used in conjunction with the procedure. In the illustrated embodiment the first cannula 100 is substantially aligned with the location at which the procedure is performed and serves as a working channel. A person skilled in the art will recognize other ways by which the procedures described herein can be performed, including through three or more cannulas, a single cannula, or through no cannula at all. Further, other types of procedures, such as open procedures, can be used in conjunction with the present disclosures.

As shown in FIG. 4A, a bone hole 108 can be formed in bone 106 using techniques known to those skilled in the art. The bone hole 108 can be disposed at a location proximate to the location at which the tendon 105 is to be attached. An anchor 80 and a suture construct 10 can then be passed through the first cannula 100 and implanted in the bone hole 108 using ordinary techniques, such as by using a driver to screw or tap the anchor into place. In the illustrated embodiment of FIG. 4B, the terminal end of the tail 16 extends from one side of the filament engagement feature 84 and out of the cannula 100 and the loop 12 extends from the other side of the filament engagement feature 84 and also out of the cannula 100. The construct 10 can be coupled to or otherwise associated with the anchor 80 prior to implantation, or it can be thread around the filament engagement feature 84 after the anchor 80 has been implanted in the bone 106.

Figure 4C:
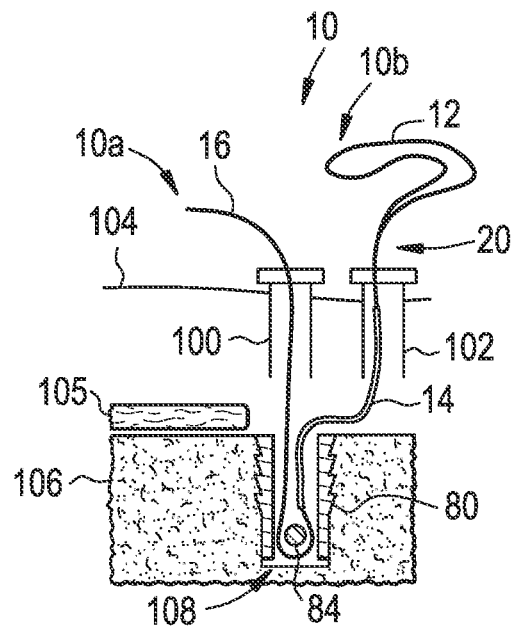

As shown in FIG. 4C, a portion of the construct 10 that includes the loop 12 can be moved to the second cannula 102. This allows for additional visibility in the working channel, and also helps a surgeon manage the two terminal ends 10a, 10b of the construct 10 so they do not become tangled and/or interchanged during portions of the procedure. Any technique known to those skilled in the art can be used to effect movement of the tail 16, and any portion of the filament 20 for that matter. In some exemplary embodiments a tool sometimes referred to as a suture grasper can be used.

Figure 4D:
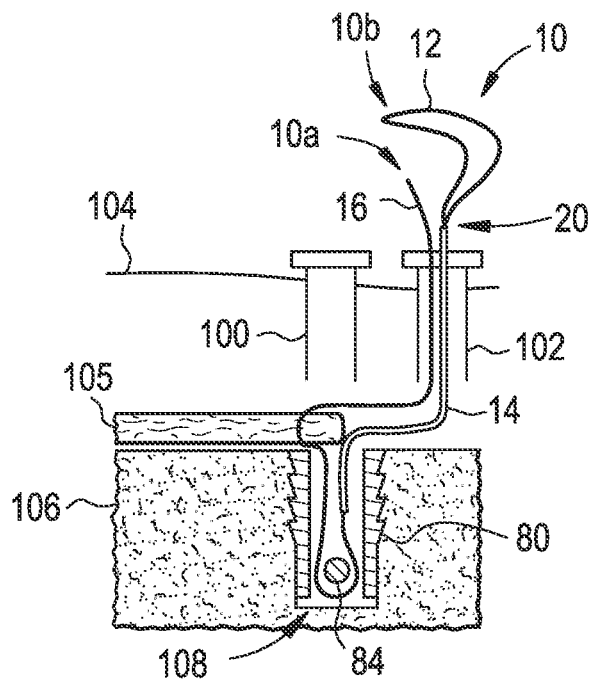

As shown in FIG. 4D, the tail 16 can be passed through the tendon 105 to be attached to bone 106 and can be passed through the second cannula 102. This results in an unobstructed view in the working channel for additional steps in the procedure. While the tail 16 can be passed through tissue using a number of techniques known to those skilled in the art, in some embodiments a suture passing device such as the EXPRESSEW II flexible suture passer, which is available from DePuy Mitek, LLC, can be passed through the first cannula 100 and operated to pass the tail 16 through the tendon 105. Furthermore, a tool such as a suture grasper can be used to move the tail 16 into the second cannula 102 after it has been passed through the tendon 105.

Figure 4E:
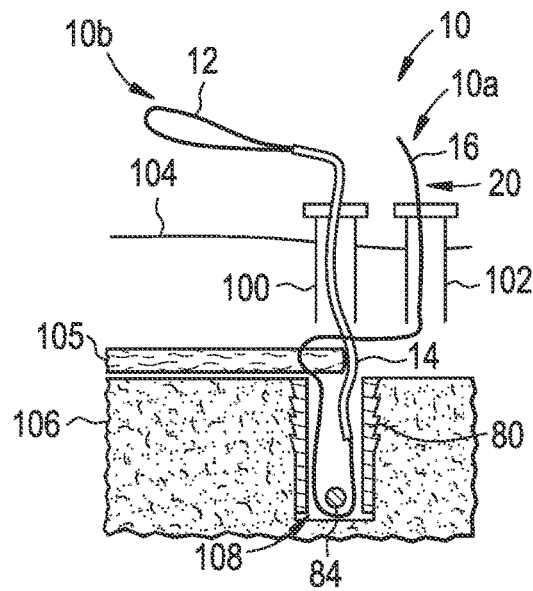
Figure 4F:
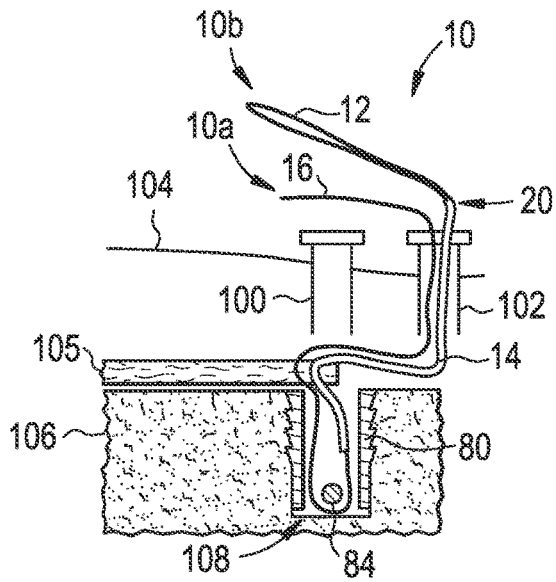

In some procedures, including some described below with respect to other illustrated embodiments, the loop 12 is not passed through tissue. However, one benefit afforded by the configuration of the present construct 10 is that it can be easily passed through tissue while minimizing an amount of trauma resulting from the same. In the present embodiment, the loop 12 is passed through tissue, as shown the tendon 105. Optionally, as shown in FIG. 4E, the loop 12 can be moved from the second cannula 102 to the first cannula 100 prior to passing the loop 12 through tendon 105. Doing so can help with suture management and prevent tangling of the filament 20 with itself or other objects disposed at or near the surgical site. The loop 12 can be passed through the tendon 105 and again back to the second cannula 102 using known techniques for passing filament through tissue. The loop 12 can pass through the tendon 105 easily because it is only the two strands of filament 20 that press through the tendon 105. There are no additional suture management components, knots, or other obstructions associated with the loop 12. The configuration that results from passing the loop 12 through the tendon 105 and into the second cannula 102 is illustrated in FIG. 4F.

Figure 4G:
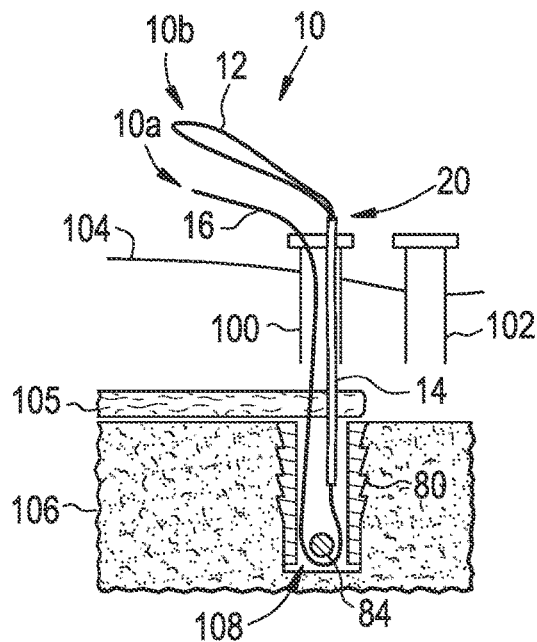
Figure 4H:
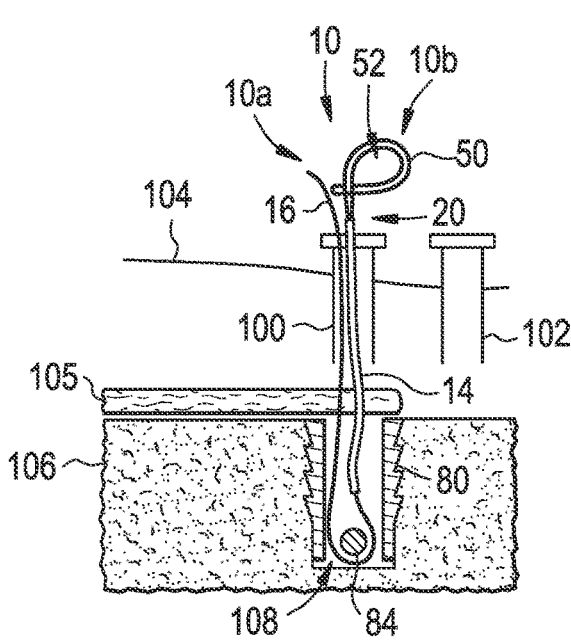
Figure 6A:
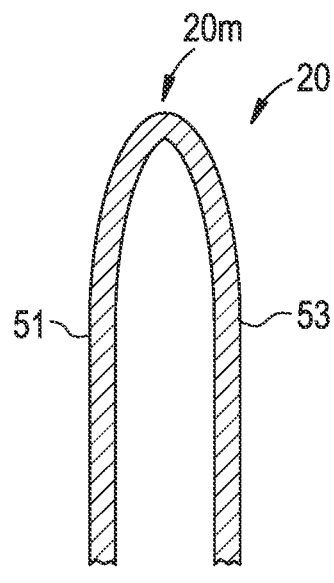
FIGS. 6A-6C are sequential, schematic views of one exemplary embodiment for forming a Lark's head cinch loop as used in the step illustrated in FIG. 4H.
Figure 6B:
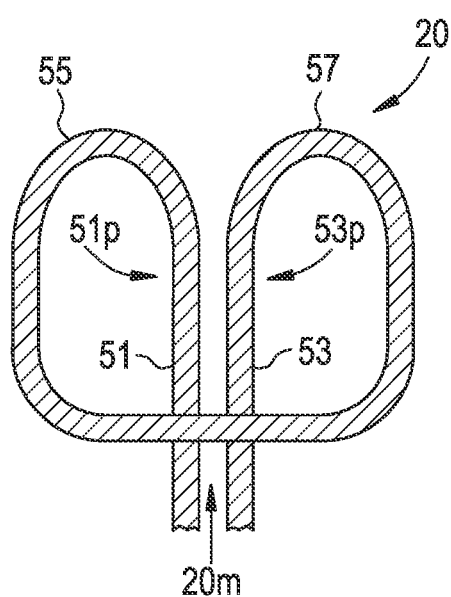
Figure 6C:
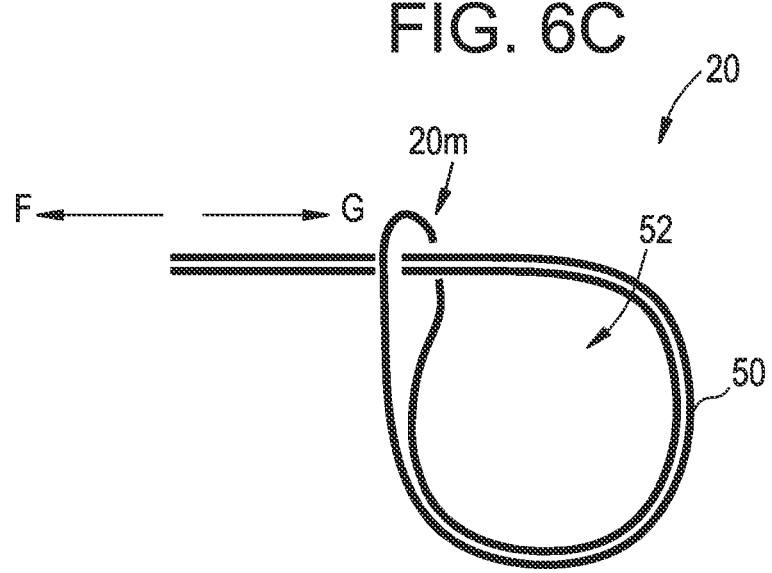

Both the loop 12 and the tail 16 can be returned to the first cannula 100 for use in the working channel, as shown in FIG. 4G. A receiving opening 52 can then be formed in the loop 12. A number of different techniques can be used to form the receiving opening, but in one exemplary embodiment, which is illustrated in FIG. 4H, a Lark's Head cinching loop 50 is formed from the filament 20 that forms the loop 12, with the Lark's Head cinching loop 50 being disposed at the distal end 10b of the construct 10. FIGS. 6A-6C, which are described in further detail below, describe one exemplary embodiment for forming a Lark's Head cinching loop, although a person skilled in the art will understand numerous techniques that can be used to form a Lark's Head cinching loop. Other types of configurations can also be used to form the receiving opening without departing from the spirit of the present disclosure.

Figure 4I:
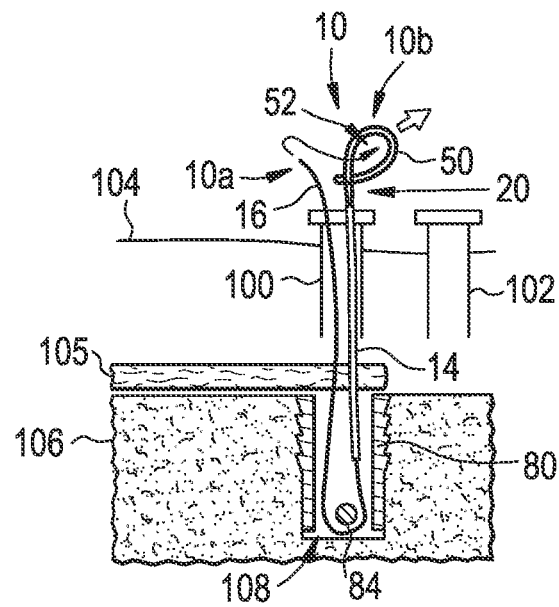
Figure 4J:
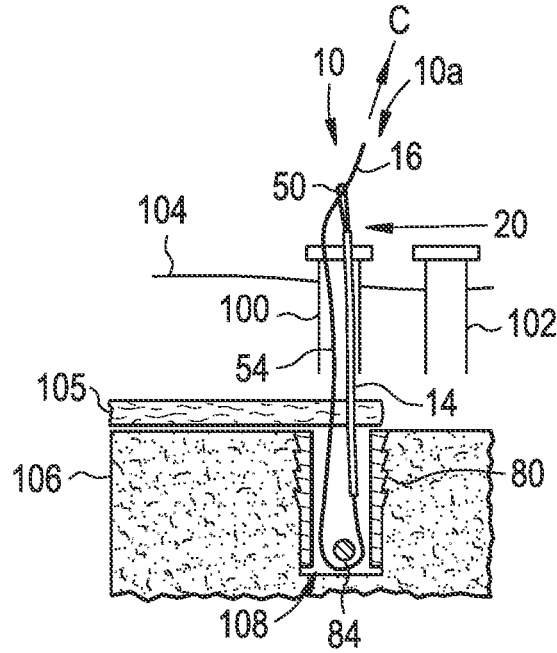
Figure 4K:
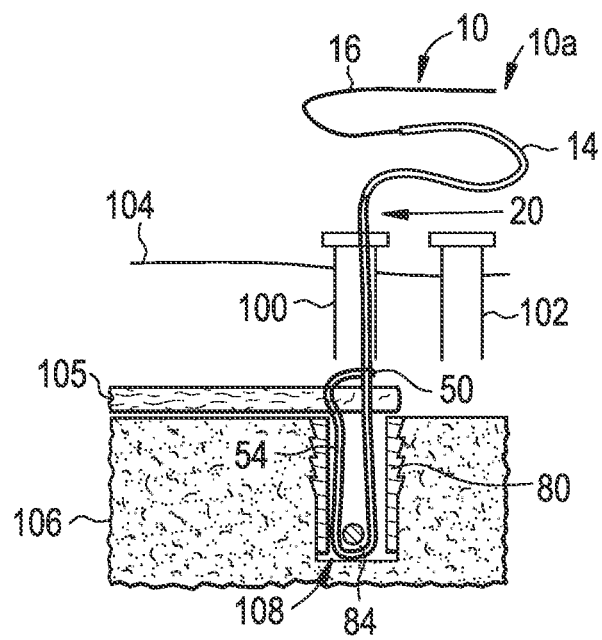

As shown in FIG. 4I, the tail 16 can be passed through the receiving opening 52 to form a collapsing loop 54 that captures the filament engagement feature 84 and the tendon 105. The Lark's Head cinching loop 50 can then be collapsed or dressed around the portion of the tail 16 disposed therethrough, as shown in FIG. 4J. Further, tension can be applied to the terminal end 10a of the construct 10 by pulling approximately in a direction C, thereby causing the collapsed Lark's Head cinch loop 50 to slide distally toward the tendon 105 in a zip-line like manner until the collapsed Lark's Head cinch loop 50 is adjacent to the tendon 105, as shown in FIG. 4K. Alternatively, tension can be applied to the terminal end 10a of the construct 10 before the Lark's Head cinch loop 50 is dressed and after the Lark's head cinch loop 50 is adjacent to the tendon, or some combination of the two actions can be used, such as partially dressing the Lark's Head cinch loop 50 before zip-lining it toward the tendon 105. In some embodiments, a knot-pushing tool can be used to assist in advancing the collapsed Lark's Head cinch loop 50 toward the tendon 105. The collapsed Lark's Head cinch loop 50 provides sufficient holding to maintain tension in the collapsing loop 54. Further, the collapsed Lark's Head cinch loop 50 provides a wider, low profile configuration that can reduce trauma to the tendon. More particularly, while the implant can be wider because of the two portions of filament extending through the tissue, the distance that the collapsed Lark's Head cinch loop 50 extends away from the tendon 105 is smaller than configurations previously relied upon for attaching tissue to bone. The configuration can also have a wide profile because portions of the filament 20 are hollow, allowing the filament 20 to become flatter with respect to the tendon 105 in which it is disposed.

Figure 4L:
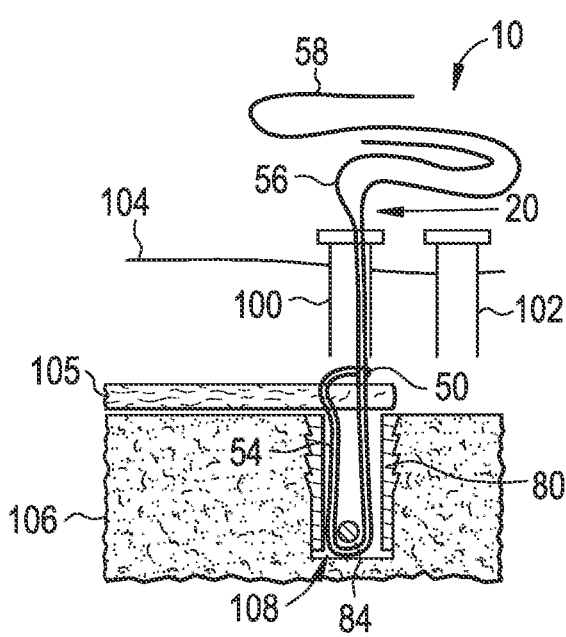

Advancing the Lark's Head cinch loop 50 toward the tendon 105 can result in the coaxial region 14 being moved out of the tissue and out of the cannula, as shown in FIG. 4K. When the coaxial region 14 is out of the tissue and exposed outside of the cannula 100, it can be easier to disassemble the coaxial region 14 and to prevent portions of the filament 20 from tangling with itself or other components associated therewith. A disassembled coaxial region is illustrated in FIG. 4L. As described above with respect to FIG. 1B, the second terminal end 20b can be untucked or pulled out of the volume of the filament 20 proximate to the opening 22. The resulting configuration is a pair of limbs 56, 58 extending out of the first cannula 100 that can be used in a variety of ways to complete a tissue attachment procedure.

Figure 4M:
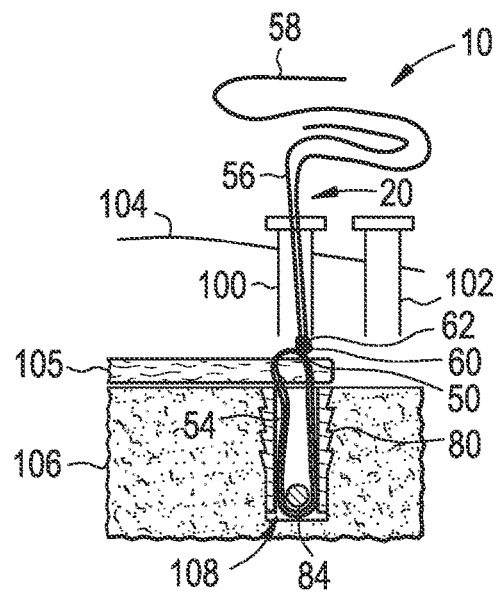
Figure 4N:
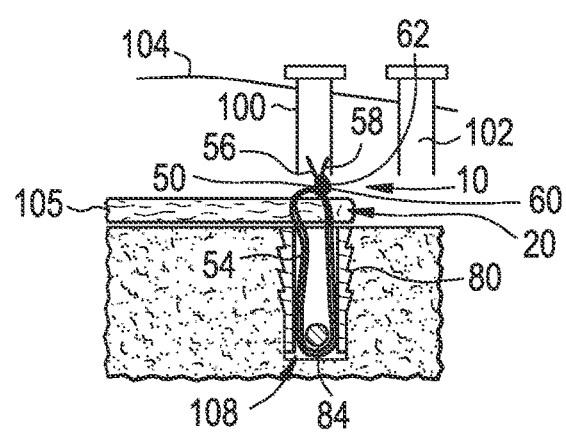

The compression afforded by the Lark's Head cinch loop 50 can hold the tendon 105 through which the construct 10 is passed at a desired location. Nevertheless, in one instance, illustrated in FIG. 4M, the limbs 56, 58 can assist in providing further security by being cinched or otherwise tied together to secure the location of the collapsed Lark's Head cinch loop 50, and thus the tendon 105, with respect to the bone 106. In the illustrated embodiment, a half-hitch 60 is formed by the surgeon using the first and second limbs 56, 58. Tying an initial half-hitch creates a one-way lock that allows for further tightening of the collapsing loop 54, i.e., by distally advancing the collapsed Lark's Head cinch loop 50, without expanding the loop, i.e., it prevents the collapsed Lark's Head cinch loop 50 for moving proximally. In some embodiments, a second half-hitch 62 can be formed to lock the location of the first half-hitch 60, thereby preventing advancement of the collapsed Lark's Head cinch loop 50 in either the distal or proximal directions. As shown in FIG. 4N, the limbs 56, 58 can be trimmed relatively close to the collapsed Lark's Head cinch loop 50 and associated half hitch(es) 60, 62 formed adjacent thereto, however, care should generally be taken not to cut the limbs 56, 58 too close to the collapsed Lark's Head cinch loop 50 so as not to affect the integrity of the collapsed Lark's Head cinch loop 50 and associated half hitch(es) 60, 62.

In addition to the aforementioned low profile configuration that results from the described procedure and variations thereof, there are numerous other advantages associated with the construct 10 and its use in surgical procedures. For instance, the resulting strength of the ending configuration is as strong and/or stronger than existing configurations known in the art. This is particularly impressive given that it takes up less space with its low profile.

The strength of the construct 10 was tested by determining a failure load for the construct, i.e., the amount of force at which the collapsing loop 54 expanded 3 millimeters or more. The tested construct was formed from a #2 Orthocord™ filament and was disposed on a 9.5 millimeter dowel pin. The collapsing loop 54 was formed from the filament using techniques described herein. Accordingly, the Lark's Head cinch loop 50 was collapsed to form the collapsing loop 54 and two half-hitches were tied on top of the collapsed cinch loop 50 to lock the location of the cinch loop 50. The resulting collapsing loop 54 had two limbs of the filament disposed adjacent to each other in a side-by-side configuration on the dowel pin. Load was then progressively applied to the collapsing loop 54 and an amount of expansion of the loop was measured as the amount of load increased. Once the collapsing loop expanded 3 millimeters or more, the amount of load applied was noted as the failure load. During testing of the aforementioned construct configuration, the failure load for the #2 Orthocord™ filament when it was coated with New Vicryl Coating was about 270 Newtons. The failure load for the #2 Orthocord™ filament when it was not coated with an additional material was about 360 Newtons Another benefit afforded by the side-by-side configuration is that it helps reduce a tendency of the filament 20 to abrade or cut through the tissue, which can occur more readily when just a single filament extends through the tissue. Still further, the configurations provided for herein are uncomplicated, and to the extent any knot tying is involved, such tying is quick and easy. This allows surgeons to perform more consistent procedures from patient-to-patient.

Figure 5A:
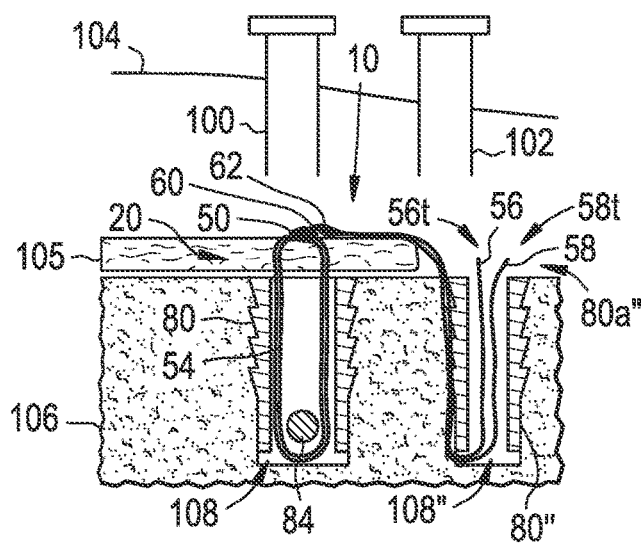
FIG. 5A is a schematic, cross-sectional view of an alternative step that can be performed in place of the step illustrated in FIG. 4N.

In some embodiments, rather than trimming the two tails 56, 58, they can be used to associate a second anchor with the first anchor 80 to form a dual-row repair. FIG. 5A represents one such configuration, which is sometimes referred to as a double row spanned repair. As shown, the tails 56, 58 extend from the one or more half-hitches 60, 62 and toward a second anchor 80" disposed in the bone 106 at a location proximate to the first anchor 80. The second anchor 80" can be disposed in the bone 106 using techniques known to those skilled in the art, including by forming a bone hole 108" in which the anchor 80" can be disposed. In this embodiment, the second anchor 80" can be a truly knotless anchor, such as a Healix Advance™ Knotless anchor or a Versalok™ anchor because of the use of the two tails 56, 58 and the anchor 80" to secure the location of the collapsed Lark's Head cinch loop 50.

As shown, the limbs 56, 58 can be placed such that as the anchor 80" is disposed in the bone hole 108", the tails 56, 58 can be pinched between an outer surface of the anchor 80" and a wall of the bone hole 108". Terminal ends 56t, 58t of the limbs 56, 58 can then be passed through the anchor 80" and back out a top side 80a" of the anchor 80" for subsequent use and/or removal. In the illustrated embodiment, the second anchor 80" is fully cannulated through a length thereof and does not include a filament engagement feature, while the first anchor 80 is also fully cannulated through its length but does include a filament engagement feature 84. A person skilled in the art will recognize that a variety of different anchor configurations can be used in conjunction with this surgical technique, and thus the illustrated embodiment of one anchor having a filament engagement feature and a second anchor being cannulated with no filament engagement feature is no way limits the scope of the present disclosure. Further, although in the illustrated embodiment the tails 56, 58 extend from the one or more half-hitches 60, 62 formed adjacent to the Lark's Head cinch loop 50, in other embodiments no half-hitches are formed and the location of the Lark's Head cinch loop 50 is instead secured by applying tension to the tails 56, 58. For example, driving the second anchor 80" into the bone hole 108" and trapping the tails 56, 58 between the anchor 80" and the bone 106 can supply sufficient tension to secure the location of the Lark's Head cinch loop 50, and thus the tendon 105 itself. Similarly, even a Lark's Head cinch loop can be eliminated such that the tension supplied to the tails 56, 58 by virtue of being pinched between the anchor 80" and the bone 106 can be sufficient to maintain a desired location in conjunction with performing a dual-row type repair. A person skilled in the art will recognize a variety of other ways by which the constructs and techniques described herein can be used in conjunction with a dual row type repair.

Figure 5B:
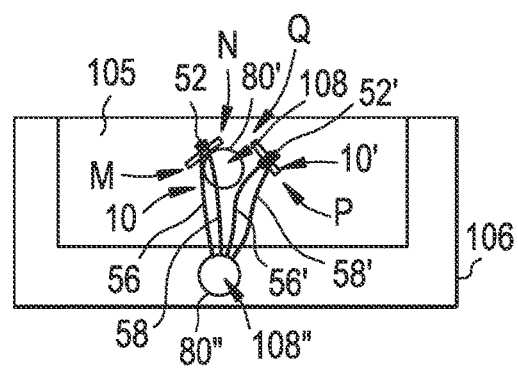
FIG. 5B is a schematic, top view of the alternative step of FIG. 5A performed in conjunction with using the construct of FIG. 3A.

FIG. 5B illustrates an alternative embodiment of using a lateral row anchor 80" to help secure the location of the constructs 10, 10' with respect to the anchor 80' of FIG. 3A. This embodiment is sometimes referred to as a double row span procedure. As shown, tails and loops of the two constructs 10, 10' can be passed through to a top side of the tissue 105 at locations M, N and P, Q, respectively, as shown. The tails of the first construct 10, 10' can then be passed through respective receiving openings 50, 50' formed in the loops of the constructs 10, 10' the receiving openings 50, 50' can be collapsed, and the receiving openings 50, 50' can be advanced toward the tissue 105 as shown using techniques previously described above. The coaxial regions of the constructs 10, 10' can be disassembled, resulting in limbs 56, 58 extending from the collapsed receiving opening 50 of the construct 10 and limbs 56', 58' extending from the collapsed receiving opening 50' of the construct 10'. The limbs 56, 58 and 56', 58' can then be trapped between the anchor 80" and bone 106 in a manner similar to as described with respect to FIG. 5A. In some embodiments, the receiving opening 50, 50' can be a Lark's Head cinch loop as described herein. While half-hitches can be used in conjunction with the Lark's Head cinch loop as described herein, the tension to the limbs 56, 58 and 56', 58' supplied by the anchor 80" can be sufficient to maintain the location of the constructs 10, 10' with respect to the anchor 80'. Further, in other embodiments, the loop itself can be the receiving openings 50, 50' and no half-hitches or other knots can be associated therewith because the location of the constructs 10, 10' with respect to the anchor 80' can be maintained by the tension supplied to the limbs 56, 58 and 56', 58' by the anchor 80".

FIGS. 6A-6C illustrate one exemplary embodiment for forming the Lark's Head cinch loop 50, which is a process that can be performed in connection with the formation of the receiving opening 52 as illustrated in FIG. 4H. As shown in FIG. 6A, the filament 20 can be folded substantially in half at an approximate midpoint 20m of the filament 20, forming a first filament limb 51 and a second filament limb 53. A central portion of the filament, which includes the midpoint 50m, can be folded toward the first and second limbs 51, 53 and brought proximate to the first and second limbs 51, 53, as shown in FIG. 6B. This results in the formation of a first sub-loop 55 and a second sub-loop 57. A size of the sub-loops 55, 57, and a length of the remaining portions of the limbs 51, 53 extending therefrom, can be adjusted as desired. The sub-loops 55, 57 can then be folded back on themselves, for instance by grasping a portion 51p, 53p of the limbs 51, 53 that are part of the sub-loops 55, 57 and pulling upward (as shown, "out of the page"). This results in the configuration illustrated in FIG. 6C, which as shown is the filament 20 having the Lark Head's cinch loop 50 formed therein with remaining portions of the first and second limbs 51, 53 extending therefrom. The Lark's Head cinch loop 50 defines the collapsible receiving opening 52, a size of which can be decreased by applying a force in an approximate direction F to one or both of the limbs 51, 53 extending from the loop 50, or by applying a force in an approximate direction G to the opening 52. Likewise, a size of the opening 52 can be increased by grasping near the midpoint 20m of the filament 20 to hold the portion where the fold is formed approximately stationary and then applying either a force in the approximate direction G to both of the limbs 51, 53 extending from the cinch loop 50, or a force in the approximate direction G to the opening 52.

A person skilled in the art will recognize other ways by which a Lark's Head cinch loop can be formed. Similarly, a person skilled in the art will be familiar with other types of cinch loop or knotted configurations, e.g., configurations having sliding knots, that can be formed from suture filaments, and will understand ways in which other techniques can be adapted for use in a manner as the Lark's Head cinch loop is used in the present disclosure. The present disclosure is not limited to use only with a Lark's Head cinch loop.

Figure 7A:
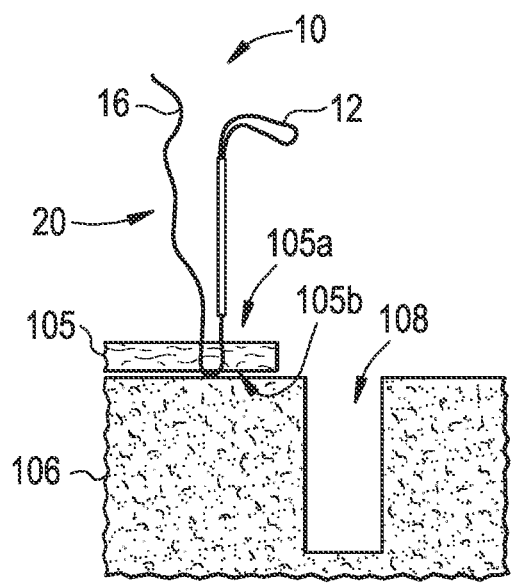
FIGS. 7A-7F are sequential, schematic, cross-sectional views of one exemplary embodiment for using the surgical repair construct of FIG. 1 to secure tissue to bone, with FIG. 7C illustrating an alternative configuration of the construct to FIG. 7B.

FIGS. 7A-7F illustrate another exemplary embodiment for using the construct 10 in a tissue repair procedure. Although not illustrated, a surgical opening can be formed through a patient's skin and one or more cannulas can be passed therethrough to create a surgical repair site in a manner similar to described above with respect to FIGS. 4A-4N and otherwise known to those skilled in the art. The cannula(s) is not shown for ease of illustration. A bone hole 108 can be formed in bone 106 using techniques known to those skilled in the art, with the bone hole 108 located at a location proximate to the location at which the tissue, which is tendon 105 in the illustrated embodiment, is to be attached. Unlike the configuration described above, in the illustrated embodiment the construct 10 is disposed through tissue prior to being associated with an anchor disposed in the bone 106. As shown in FIG. 7A, the tissue is passed through the tissue such that both the tail 16 and the loop 12 extend proximally toward the surgeon for use during the procedure. The construct 10 can be associated with the tendon 105 using a variety of techniques, including by threading the tail 16 through the tissue from a top side 105a to a bottom side 105b, and then back again from the bottom side 105b to the top side 105a. In an alternative embodiment, both the tail 16 and the loop 12 can be passed through the tendon 105 to achieve the configuration illustrated in FIG. 7A.

Figure 7B:
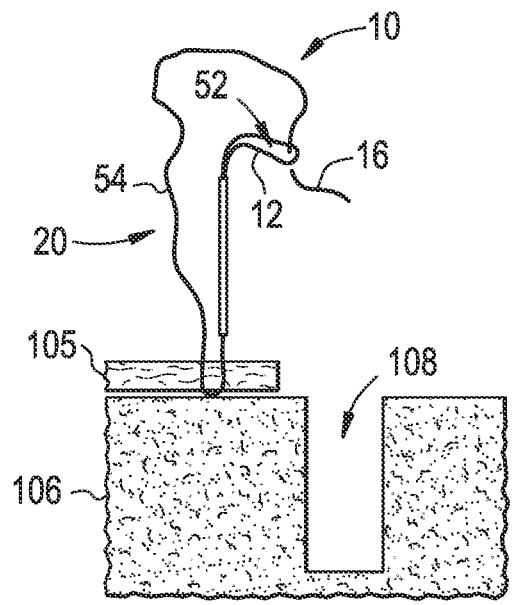
Figure 7C:
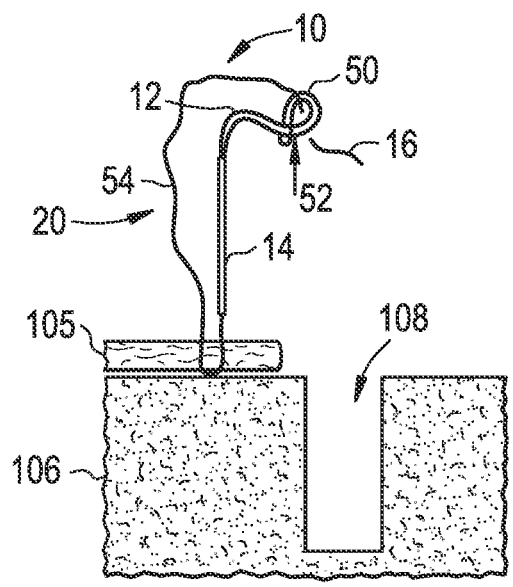
Figure 7D:
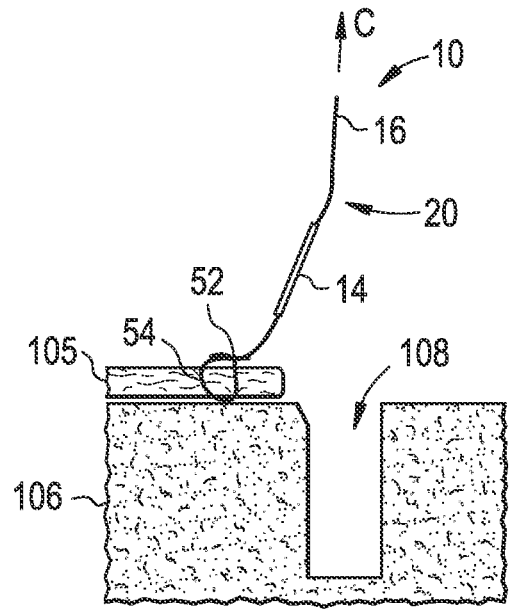

The tail 16 can then be passed through the loop 12, as shown in FIG. 7B. Alternatively, as shown in FIG. 7C, the loop 12 can be formed into a Lark's Head cinch loop 50 using techniques previously described, or others known to those skilled in the art, and then the tail 16 can be passed through the receiving opening 52 defined by the cinch loop 50. In either configuration, passing the tail 16 through the loop 12 or receiving opening 52 results in the formation of a collapsing loop 54. As described above, the Lark's Head cinch loop 50 can be collapsed or dressed around the portion of the tail 16 disposed therethrough. Likewise, to the extent that the loop 12 is adjustable, a person skilled in the art would recognize ways by which the loop 12 could be collapsed around the portion of the tail 16 disposed therethrough. As shown in FIG. 7D, tension can be applied to the terminal end 10a of the construct 10 by pulling approximately in a direction C, thereby causing the loop 12 (FIG. 7B) or Lark's Head cinch loop 50 (FIG. 7C) to slide distally toward the tendon 105 in a zip-line like manner until the loop 12 or Lark's Head cinch loop 50 is adjacent to the tendon 105. The collapsed loop 12 and the collapsed Lark's Head cinch loop 50 provide sufficient holding to maintain tension in their respective collapsing loops 54.

Figure 7E:
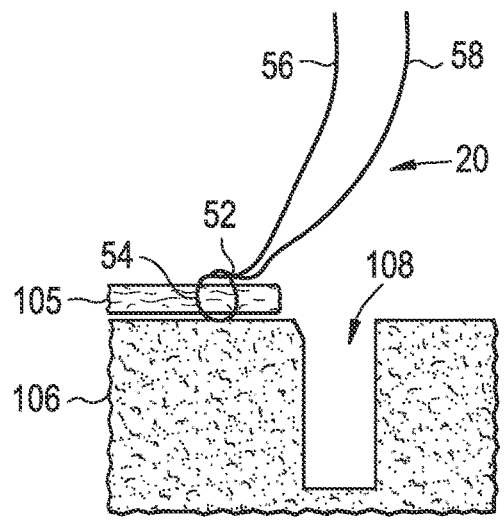
Figure 7F:
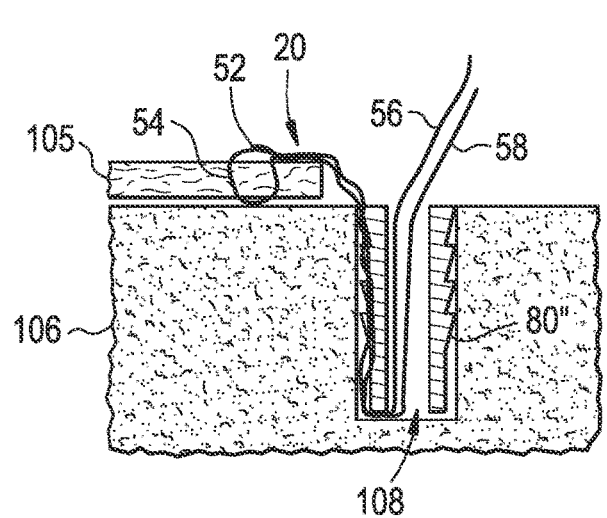
Figure 8:
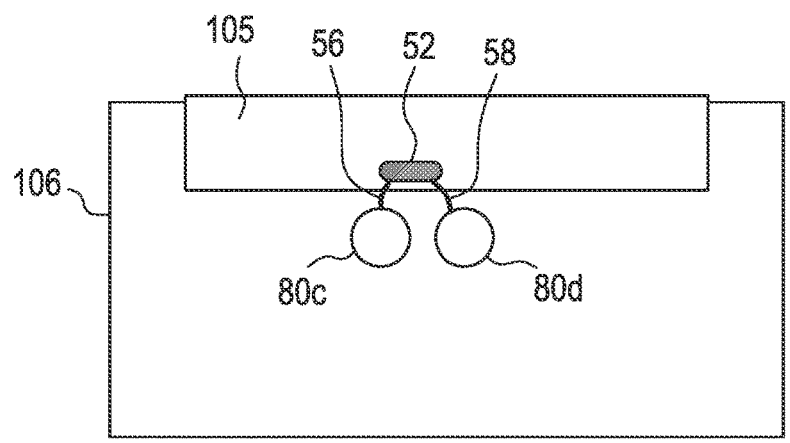
FIG. 8 is a schematic, top view of another exemplary embodiment for using the surgical repair construct of FIG. 1 to secure tissue to bone.

The coaxial region 14 of the construct 10 can subsequently be disassembled, as shown in FIG. 7E. More specifically, a second terminal end of the filament 20 can be untucked or pulled out of the volume of the filament 20 proximate to an opening of the filament 20, as described above with respect to FIG. 1B. The resulting configuration is a pair of limbs 56, 58 that can be used in a variety of ways to complete a tissue attachment procedure. By way of non-limiting example, FIG. 7F illustrates the limbs 56, 58 extending to an anchor 80''' disposed in the bone hole 108 in a manner as described previously with respect to FIG. 5. In an alternative embodiment, illustrated in FIG. 8, the limb 56 can extend from the collapsed Lark's Head cinch loop 50 associated with the anchor 80''' (not shown) located in a medial or primary fixation row to an anchor 80c located in a lateral row, while the limb 58 can extend from the collapsed Lark's Head cinch loop 50 to an anchor 80d also located in the lateral row. Tension can be applied to the limbs 56, 58 by the respective anchors 80c, 80d, or using other techniques known to those skilled in the art, thereby maintain a location of the collapsed receiving opening with respect to the anchor 80'''. While as described with respect to FIG. 8 the Lark's Head cinch loop 50 is associated with an anchor, in other embodiments the collapsed Lark's Head cinch loop 50 can be associated with the tissue 105 on its own, i.e., without an anchor, using techniques disclosed herein or otherwise known to those skilled in the art.

FIGS. 9-15 illustrate some further, non-limiting types of tissue securing procedures that can be performed using the constructs and related disclosures provided for herein. The constructs can lead to procedures that are faster, easier, and more durable than existing tissue repair procedures.

Figure 9:
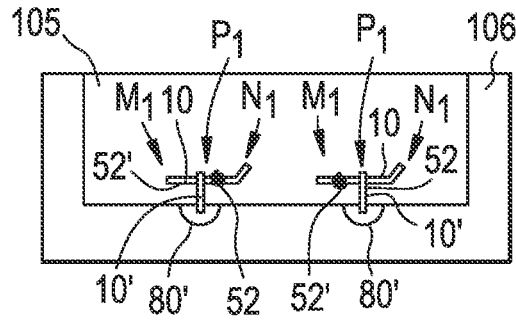
FIG. 9 is a schematic, top view of one exemplary embodiment for using the surgical repair construct of FIG. 3A to secure tissue to bone.

FIG. 9 illustrates one exemplary embodiment of a single row repair. As shown, two anchors 80' are double-loaded such that they both include two constructs 10, 10' coupled thereto. The anchors 80' are disposed in bone 106 using techniques known to those skilled in the art. The loop and tail of one of the constructs 10 associated with each anchor 80' can be passed through to a top side of the tissue 105 at locations $M_1$ and $N_1$ as shown. The tail can then be passed through a receiving opening 52 formed in the loop, the receiving opening 52 can be collapsed, and the collapsed receiving opening 52 can be advanced toward the tissue 105 using techniques described herein. Further, the tail of the other construct 10' can be passed through to a top side of the tissue 105 at a location $P_1$ as shown, for engagement with the loop associated with the anchor 80'. The tail can then be passed through a receiving opening 52' formed in the loop, the receiving opening 52' can be collapsed, and the collapsed receiving opening 52' can be advanced toward the tissue 105 as shown using techniques previously described above. The location P₁ is such that when the tail and loop are coupled together via the receiving opening 52', the combination of the tail and loop of the first construct 80 is disposed between the tissue 105 and the combination of the tail and loop of the second construct 10'. As a result, the combination of the tail and the loop of the first construct 10 can serve as a rip stop or cruciate stitch to help prevent tissue tearing by the other construct 10'.

Figure 10:
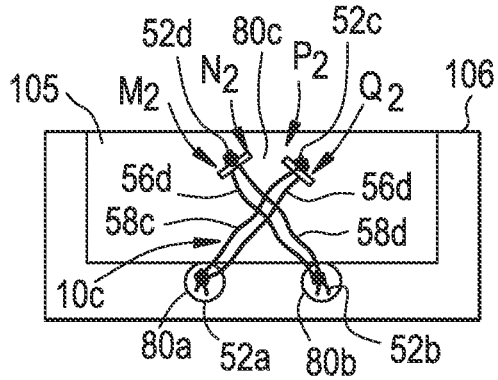
FIG. 10 is a schematic, top view of one exemplary embodiment for using the surgical repair construct of FIG. 2.

FIG. 10 illustrates one exemplary embodiment of a lateral row anchor repair using two anchors 80a, 80b disposed in bone 106 in a lateral row, each anchor 80a, 80b having a single construct 10a, 10b associated therewith, and two additional constructs 10c, 10d extending from the medial or primary fixation row. In the illustrated embodiment the third and fourth constructs 10c and 10d are double-loaded onto an anchor 80c, although in other embodiments each construct can be associated with its own anchor, or the constructs 10c, 10d can be coupled to tissue without use of an anchor using techniques described herein or otherwise known to those skilled in the art. The anchors 80a, 80b, 80c are configured like the anchor 80 of FIG. 2, and the constructs 10a, 10b, 10c, and 10d are configured like the construct 10 of FIG. 2, but the addition of the letters "a," "b," "c," and "d" are included for identification purposes of the separate implants.

As shown, the anchors 80a, 80b are disposed in the bone 106 in a lateral row, with the constructs 10a, 10b each having a loop and a tail as described herein. The loop for each construct 10a, 10b can be configured to receive portions of the third or fourth constructs 10c, 10d, as well as the tail of its own construct 10a, 10b. For example, a Lark's Head cinch loop can form a receiving opening 52a, 52b in the loop to receive the third or fourth constructs 10c, 10d and the respective construct tail and collapse around them. Alternatively, the loop can have another collapsible configuration that is capable of collapsing around a construct 10c, 10d and the tail of the respective construct 10a, 10b of the loop.

In the illustrated embodiment, the loop and tail of the construct 10c can be passed through to a top side of the tissue 105 at locations M₂ and N₂ as shown. Likewise, the loop and tail of the construct 10d can be passed through to a top side of the tissue 105 at locations P₂ and Q₂ as shown. The tail of the respective construct 10c, 10d can then be passed through its own receiving opening 52c, 52d formed in its loop, the receiving opening 52c, 52d can be collapsed, and the collapsed receiving opening 52c, 52d can be advanced toward the tissue 105 using techniques described herein. The coaxial region of the tails of the constructs 10c, 10d can be disassembled into limbs 56c, 58c and 56d, 58d. Optionally, one or more half-hitches can be formed using the limbs 56c, 58c and 56d, 58d. Regardless of whether any half-hitches are formed, the limbs 56c, 58c, and 56d, 58d can be extended towards the lateral row anchors 80a, 80b. In the illustrated embodiment the limbs 56c, 58c, and 56d, 58d are extended in a crossing manner such that the limbs 56c, 58c extend to the anchor 80a that is on the opposite side of the medial anchor 80c, and the limbs 56d, 58d extend to the anchor 80b that is also on the opposite side of the medial anchor 80d. A person skilled in the art will recognize that other configurations for associating the limbs 56c, 58c and 56d, 58d with the anchors 80a, 80b can also be used.

As shown, the receiving opening 52a associated with the anchor 80a can receive the limbs 56c, 58c, as well as the tail of the construct 10a, and then the receiving opening 52a can be collapsed or dressed to capture the limbs 56c, 58c and the tail. Likewise, the receiving opening 52b associated with the anchor 80b can receive the limbs 56d, 58d, as well as the tail of the construct 10b, and then the receiving opening 52b can be collapsed or dressed to capture the limbs 56d, 58d and the tail. A pulling force can be applied to the respective tails, which in turn can pull the collapsed receiving openings 52a, 52b onto the respective anchors 80a, 80b. The coaxial region of the tails of the constructs 10a, 10b can be disassembled and used to form one or more half-hitches. While the half-hitches can set the location of the receiving openings 52a, 52b with respect to the anchors 80a, 80b, the limbs 56c, 58c and 56d, 58d of the constructs 10c, 10d can still be slid through the respective openings 52a, 52b. The limbs 56c, 58c and 56d, 58d can be used to form one or more half-hitches to set the location of the limbs 56c, 58c and 56d, 58d to prevent them from sliding.

Figure 11:
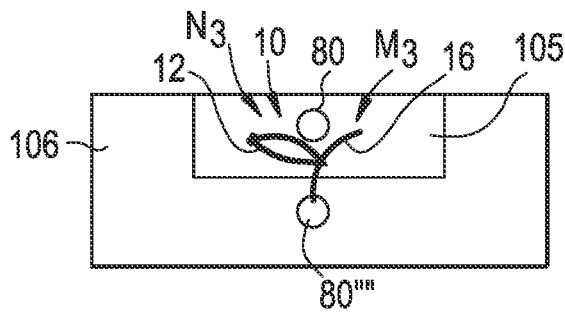
FIG. 11 is a schematic, top view of still another exemplary embodiment for using the surgical repair construct of FIG. 2.

FIG. 11 illustrates one exemplary embodiment of using the construct 10 and anchor 80 of FIG. 2 in a tissue repair procedure. As shown, the anchor 80 having the construct 10 associated therewith is implanted in bone 106 in a medial or primary fixation row. The tail 16 of the construct 10 passes through the tissue 105 to a top side of the tissue at a location M₃ and the loop 12 of the construct 10 passes through the tissue 105 to a top side of the tissue at a location N₃. The tail 16 is passed through a portion of the loop 12, and is then extended to an anchor 80'''' disposed in the lateral row in the bone 106. Tension is applied to the tail 16, and thus the rest of the construct 10, by trapping the tail 16 between the anchor 80'''' and the bone 106. As a result, the formation of a Lark's Head cinch loop and/or half-hitches can be optional.

Figure 12:
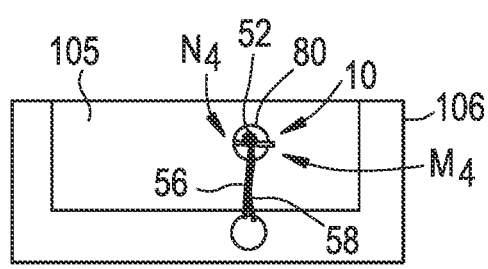
FIG. 12 is a schematic, top view of yet another exemplary embodiment for using the surgical repair construct of FIG. 2.

FIG. 12 illustrates another exemplary embodiment of using the construct 10 and anchor 80 of FIG. 2 in a tissue repair procedure. In this embodiment, a thicker footprint can be achieved by using a thicker filament 20, such as a #5 Ethibond™ filament. As shown, the anchor 80 having the construct 10 associated therewith can be implanted in a medial or primary fixation row. The loop and tail of the construct 10 can be passed through tissue 105 to a top side of the tissue at locations M₄ and N₄, and the tail can then be passed through the receiving opening 52 formed by the loop, such as a Lark's Head cinch loop. The receiving opening 52 can be collapsed around the tail, and then a coaxial region of the construct 10 can be deconstructed as described herein. The limbs 56, 58 that result from the deconstruction of the coaxial region can extend side-by-side to an anchor in the lateral row for subsequent attachment. Because the filament 20 is of a thicker variety, the configuration of the construct 10 can be of a ribbon-like footprint.

Figure 13:
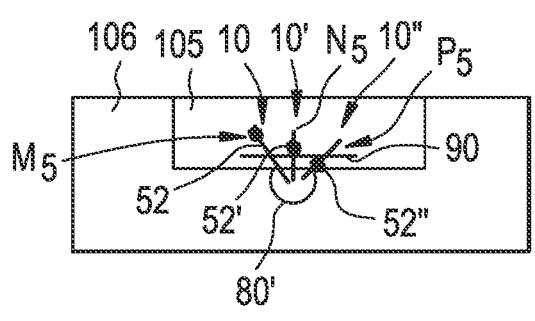
FIG. 13 is a schematic, top view of one exemplary embodiment for using the surgical repair construct of FIG. 3B.

FIG. 13 illustrates one exemplary embodiment of using the anchor 80' in conjunction with the three constructs 10, 10', and 10' illustrated in FIG. 3B. In this embodiment, thinner filaments 20 can be used to more easily allow for all three constructs 10, 10', 10" to be operated without tangling or other undesirable obstructions. As shown, the tails can be passed through tissue 105 to a top side of the tissue at locations M₅, N₅, and P₅, to engage with the loops associated with the anchor 80". The tails can then be passed through a receiving opening 52, 52', 52" formed by the loops, such as Lark's Head cinch loops. The receiving openings 52, 52', 52" can then be collapsed around the respective tails. The coaxial region can be deconstructed and then the limbs resulting therefrom can be used to tie one or more half-hitches to maintain a location of the collapsed receiving openings 52, 52', 52" using techniques described herein or otherwise known to those skilled in the art. In some embodiments, a rip stitch 90 can be disposed laterally across a portion of the tissue 105 to receive the collapsed receiving openings 52, 52', 52". The rip stitch 90 can prevent undesirable tearing due to stress caused by the collapsed receiving openings 52, 52', 52".

Figure 14:
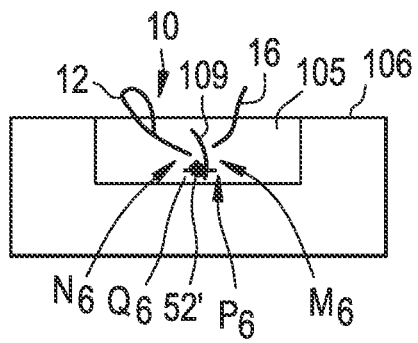
FIG. 14 is a schematic, top view of one exemplary embodiment for using the surgical repair construct of FIG. 1A in conjunction with the surgical repair construct of FIG. 2.

FIG. 14 illustrates one exemplary embodiment for repairing a tear 109 in tissue 105. In the illustrated embodiment, the construct 10, 10' is used in two different ways to repair the tear 109. In one instance, the construct 10 is used by itself, without any attachment to any anchor or other implant device. The tail 16 and the loop 12 can extend from opposite sides of the tear 109 at locations $M_6$ and $N_6$ as shown. Then the construct 10 can be operated in a manner similar to as described herein for other embodiments. For example, a receiving opening can be formed from the loop 12, the tail 16 can be disposed in the receiving opening, and the receiving opening can be collapsed or dressed around the tail 16. Tension can then be applied to the tail 16 to advance the collapsed receiving opening against the tissue 105, and thus adjacent to the tear 109. As the receiving opening is collapsed, the portions of tissue 106 through which the tail 16 and loop 12 are disposed can be drawn towards each other.

In the other instance, the construct 10' is used in conjunction with an anchor (not shown) disposed in bone 106. The tail and the loop extend from opposite sides of the tear 109 at locations $P_6$ and $Q_6$ as shown. Then the construct 10' is operated as described with respect to the first instance in FIG. 14. The illustrated embodiment shows the collapsed receiving opening 52' with the tail disposed therethrough adjacent to the tear 109 and one or more half-hitches formed therein to lock the location of the collapsed receiving opening 52' with respect to the tear 109. Using the construct 10' with the anchor provides for a secure attachment of the torn tissue 105 to bone 106 while also providing repair to the tear 109 itself. Use of the construct 10 without the anchor can be used to help repair the tear 109 even without attaching to bone, for example in instances in which the tear is located too far away from the bone to effectively use an anchor.

Figure 15:
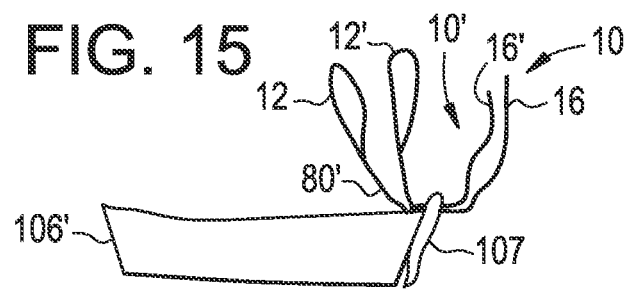
FIG. 15 is a schematic, side view of another exemplary embodiment for using the surgical repair construct of FIG. 3A.

FIG. 15 illustrates one exemplary embodiment of using the dual-loaded anchor 80' of FIG. 3A in an instability repair involving a glenoid or hip 106' and labral tissue 107. As shown, the anchor 80' is implanted in the hip 106' using techniques known to those skilled in the art. Each of the two tails 16, 16' are then passed from one side of the labral tissue 107 to the other side. The loops 12, 12' remain disposed on the same side of the labral tissue as the anchor 80'. The tails 16, 16' and loops 12, 12' are then operated using techniques described herein or otherwise known to those skilled in the art. For example, a collapsible receiving opening can be formed in the loop 12, 12' and the receiving opening can receive the tail 16, 16'. The tail 16, 16' can then be operated to advance the collapsed receiving opening toward the anchor 80', which in turn draws the labral tissue 107 toward the hip 106'. The resulting collapsed receiving opening can be held in place by some combination of a Lark's Head cinching loop (if used to form the receiving opening for instance), one or more half-hitches, or extending limbs from a disassembled coaxial region toward another anchor to apply tension to the limbs.

One skilled in the art will appreciate further features and advantages of the invention based on the above-described embodiments. Accordingly, the invention is not to be limited by what has been particularly shown and described, except as indicated by the appended claims. A person skilled in the art would be able to adapt the constructs, anchors, and techniques provided for herein for suitable use with other combinations of constructs, anchors, and techniques without departing from the spirit of the present disclosure. Further, although the constructs and methods provided for herein are generally directed to surgical techniques, at least some of the constructs and methods can be used in applications outside of the surgical field. All publications and references cited herein are expressly incorporated herein by reference in their entirety.

What is claimed is:

1. A surgical repair method, comprising:
    passing a terminal end of a surgical filament through soft tissue at a location proximate to bone in which the soft tissue is to be attached, the surgical filament having a first portion with a loop formed therefrom, the loop including a snare formed from a portion thereof, a second portion that includes the terminal end, and a coaxial region formed between the first and second portions by disposing a portion of the filament into its own volume, the terminal end and the loop extending proximally from the soft tissue;
    passing the terminal end of the second portion through the snare;
    collapsing the snare to engage the soft tissue;
    deconstructing the coaxial region by removing the portion of the filament from the volume of the filament in which it was disposed;
    associating the surgical filament with an anchor disposed in the bone; and
    advancing the collapsed snare distally to bring the tissue into proximity with the bone.

2. The method of claim 1, further comprising forming the snare from the loop of the first portion of the filament after passing the terminal end of a surgical filament through soft tissue.

3. The method of claim 1, further comprising inserting the anchor in bone in proximity to the soft tissue.

4. The method of claim 1, wherein passing the terminal end through soft tissue comprises passing the terminal end through the soft tissue from a proximal side to a distal side and then back through the soft tissue again to the proximal side.

5. The method of claim 1, wherein passing the terminal end through soft tissue comprises separately passing the terminal end and the loop through the soft tissue from a distal side to a proximal side.

6. The method of claim 1, wherein deconstructing comprises removing a second terminal end of the filament out of the volume out from the volume of the filament in which it was disposed such that the second terminal end extends proximally from the soft tissue.

7. The method of claim 1, wherein advancing the collapsed snare distally to bring the tissue into proximity with the bone comprises trapping the surgical filament between the anchor and bone and inserting the anchor into bone, the inserting tensioning the surgical filament to advance the collapsed snare distally.

8. The method of claim 1, wherein the anchor is a first anchor, the method further comprising, after associating the surgical filament with the first anchor disposed in bone, associating the surgical filament with a second anchor disposed in bone at a location proximate to the first anchor.

9. The method of claim 8, further comprising, associating the surgical filament with a second anchor and disposing the second anchor in bone at a location proximate to the first anchor, wherein disposing the second anchor in bone comprises trapping the surgical filament between the second anchor and bone.

10. The method of claim 9, wherein trapping the surgical filament between the second anchor and bone comprises tensioning the surgical filament and further collapsing the snare.

11. The method of claim 1, further comprising tying at least one locking knot with the filament at a location that is proximate to the collapsed snare to secure a location of the filament with respect to the tissue.

12. A surgical repair method, comprising:
passing a first terminal end of a surgical filament through soft tissue at a location proximate to bone in which the soft tissue is to be attached, the surgical filament having a first portion that includes the first terminal end, a second portion that includes a loop formed therefrom and a second terminal end, and a coaxial region formed between the first and second portions, by disposing the second terminal end of the surgical filament into its own volume, the first terminal end and the loop extending proximally from the soft tissue, and the loop of the second portion arranged to form cinch loop defining a receiving opening;
passing the first terminal end of the surgical construct through the receiving opening;
collapsing the receiving opening of the cinch loop;
deconstructing the coaxial region by removing the second terminal end of the surgical filament from the volume of the surgical filament in which it was disposed; and
associating the surgical filament with an anchor disposed in the bone; and
advancing the collapsed cinch loop distally to bring the tissue into proximity with the bone.

13. The method of claim 12, further comprising forming the cinch loop in the second terminal end of the first surgical filament after the first terminal end has been passed through the soft tissue.

14. The method of claim 12, further comprising tying at least one locking knot with the filament at a location that is proximate to the collapsed snare to secure a location of the filament with respect to the tissue.

15. The method of claim 12, further comprising inserting the anchor in bone in proximity to the soft tissue.

16. The method of claim 12, wherein passing the first terminal end through soft tissue comprises passing the first terminal end through the soft tissue from a proximal side to a distal side and then back through the soft tissue again to the proximal side.

17. The method of claim 12, wherein passing the first terminal end through soft tissue comprises separately passing the first terminal end and the loop through the soft tissue from a distal side to a proximal side.

18. The method of claim 12, wherein advancing the collapsed cinch loop distally to bring the tissue into proximity with the bone comprises trapping the surgical filament between the anchor and bone and inserting the anchor into bone, the inserting tensioning the surgical filament to advance the collapsed cinch loop distally.

19. The method of claim 12, wherein the anchor is a first anchor, the method further comprising, after associating the surgical filament with the first anchor disposed in bone, associating the surgical filament with a second anchor disposed in bone at a location proximate to the first anchor.

20. The method of claim 19, further comprising, associating the surgical filament with a second anchor and disposing the second anchor in bone at a location proximate to the first anchor, wherein disposing the second anchor in bone comprises trapping the surgical filament between the second anchor and bone.

21. The method of claim 20, wherein trapping the surgical filament between the second anchor and bone comprises tensioning the surgical filament and further collapsing the snare.

22. The method of claim 12, further comprising:
removing the second terminal end of the surgical filament from the coaxial region of the filament after collapsing the receiving opening of the cinch loop; and
tying at least one knot with the filament at a location that is proximate to the collapsed cinch loop to secure a location of the filament with respect to the tissue.

23. The method of claim 12, wherein the surgical filament is associated with the anchor disposed in the bone after passing the first terminal end through the receiving opening.

* * * * *